(12) United States Patent
Cave et al.

(10) Patent No.: US 12,131,397 B2
(45) Date of Patent: *Oct. 29, 2024

(54) SYSTEM, METHOD, AND GRAPHICAL USER INTERFACE FOR IDENTIFYING MEDICAL CARE PROVIDERS OUTSIDE A PROCESS-OF-CARE STANDARD

(71) Applicant: EFFINET, LLC, San Mateo, CA (US)

(72) Inventors: Douglas G. Cave, San Mateo, CA (US); Yuri Alexandrian, San Ramon, CA (US); John Calvin, Mountain View, CA (US)

(73) Assignee: EFFINET, LLC, San Mateo, CA (US)

( * ) Notice: Subject to any disclaimer, the term of this patent is extended or adjusted under 35 U.S.C. 154(b) by 166 days.

This patent is subject to a terminal disclaimer.

(21) Appl. No.: 17/665,847

(22) Filed: Feb. 7, 2022

(65) Prior Publication Data
US 2022/0156867 A1    May 19, 2022
US 2024/0303761 A9    Sep. 12, 2024

Related U.S. Application Data

(63) Continuation of application No. 17/039,309, filed on Sep. 30, 2020, now Pat. No. 11,244,416, which is a
(Continued)

(51) Int. Cl.
*G16H 40/20*    (2018.01)
*G06Q 10/0639*    (2023.01)
*G06Q 50/22*    (2018.01)

(52) U.S. Cl.
CPC ....... *G06Q 50/22* (2013.01); *G06Q 10/06393* (2013.01); *G16H 40/20* (2018.01)

(58) Field of Classification Search
CPC ... G06Q 50/22–24; G16H 40/20; G16H 15/00
See application file for complete search history.

(56) References Cited

U.S. PATENT DOCUMENTS 4,489,387 A    12/1984    Lamb et al.
4,491,725 A    1/1985    Pritchard
(Continued)

OTHER PUBLICATIONS

W. Welch et al., "Geographic Variation in Expenditures for Physicians' Services in The United States," The New England Journal of Medicine, vol. 328, No. 9, pp. 621-627, Mar. 1994.
(Continued)

*Primary Examiner* — John A Pauls
(74) *Attorney, Agent, or Firm* — Armstrong Teasdale LLP

(57) ABSTRACT

A computer system for identifying medical care providers outside a process-of-care standard for a field of health care is configured to perform steps that include retrieving claim line item information including procedure/service codes, and retrieving definitions for marker code groups associated with each of a set of medical conditions; deriving, for each marker-condition pair, an actual rate of utilization of the marker code group for episodes of the associated medical condition; and assigning a status to each marker-condition pair in response to the actual rate of utilization respectively exceeding or not exceeding a target rate. The steps also include aggregating the statuses across the marker-condition pairs to obtain an overall score, and causing an output to be displayed in a viewable format. The output includes the overall score, each marker-condition pair of the set of medical conditions, and the status for each marker-condition pair of the set of medical conditions.

20 Claims, 14 Drawing Sheets

Related U.S. Application Data continuation-in-part of application No. 15/162,217, filed on May 23, 2016, now Pat. No. 10,867,361, which is a continuation of application No. 14/172,728, filed on Feb. 4, 2014, now abandoned, which is a continuation-in-part of application No. 13/621,222, filed on Sep. 15, 2012, now Pat. No. 8,751,263, and a continuation of application No. 13/970,564, filed on Aug. 19, 2013, now abandoned, which is a continuation-in-part of application No. 13/621,222, filed on Sep. 15, 2012, now Pat. No. 8,751,263, which is a continuation of application No. 12/473,147, filed on May 27, 2009, now Pat. No. 8,301,464.

(60) Provisional application No. 61/867,577, filed on Aug. 19, 2013, provisional application No. 61/082,080, filed on Jul. 18, 2008.

(56) References Cited

U.S. PATENT DOCUMENTS

| | | | |
|---|---|---|---|
| 4,667,292 A | 5/1987 | Mohlenbrock et al. | |
| 4,858,121 A | 8/1989 | Barber et al. | |
| 4,878,175 A | 10/1989 | Norden-Paul et al. | |
| 4,937,743 A | 6/1990 | Rassman et al. | |
| 4,987,538 A | 1/1991 | Johnson et al. | |
| 5,001,630 A | 3/1991 | Wiltfong | |
| 5,018,067 A | 5/1991 | Mohlenbrock et al. | |
| 5,065,315 A | 11/1991 | Garcia | |
| 5,070,452 A | 12/1991 | Doyle, Jr. et al. | |
| 5,072,383 A | 12/1991 | Brimm et al. | |
| 5,099,424 A | 3/1992 | Schneiderman | |
| 5,225,976 A | 7/1993 | Tawil | |
| 5,235,702 A | 8/1993 | Miller | |
| 5,253,164 A | 10/1993 | Holloway et al. | |
| 5,301,105 A | 4/1994 | Cummings, Jr. | |
| 5,307,262 A | 4/1994 | Ertel | |
| 5,319,543 A | 6/1994 | Wilhelm | |
| 5,324,077 A * | 6/1994 | Kessler | B42D 25/29 283/54 |
| 5,325,293 A | 6/1994 | Dorne | |
| 5,359,509 A | 10/1994 | Little et al. | |
| 5,365,425 A | 11/1994 | Torma et al. | |
| 5,392,209 A | 2/1995 | Eason et al. | |
| 5,404,292 A | 4/1995 | Hendrickson | |
| 5,467,268 A | 11/1995 | Sisley et al. | |
| 5,471,382 A | 11/1995 | Tallman et al. | |
| 5,483,443 A | 1/1996 | Milstein et al. | |
| 5,486,999 A | 1/1996 | Mebane | |
| 5,519,607 A | 5/1996 | Tawil | |
| 5,557,514 A | 9/1996 | Seare et al. | |
| 5,583,758 A | 12/1996 | McIlroy et al. | |
| 5,664,207 A | 9/1997 | Crumpler et al. | |
| 5,724,379 A | 3/1998 | Perkins et al. | |
| 5,835,897 A | 11/1998 | Dang | |
| 5,970,463 A | 10/1999 | Cave et al. | |
| 6,223,164 B1 | 4/2001 | Seare et al. | |
| 7,739,126 B1 | 6/2010 | Cave et al. | |
| 8,301,464 B1 | 10/2012 | Cave et al. | |
| 8,751,263 B1 | 6/2014 | Cave et al. | |
| 9,179,061 B1 | 11/2015 | Kraft et al. | |
| 10,319,474 B1 | 6/2019 | Cave et al. | |
| 10,685,746 B2 | 6/2020 | Cave et al. | |
| 10,867,361 B1 | 12/2020 | Cave et al. | |
| 11,244,416 B2 | 2/2022 | Cave et al. | |
| 2004/0111291 A1 | 6/2004 | Dust et al. | |
| 2004/0236605 A1* | 11/2004 | Somani | G06Q 40/08 705/2 |
| 2006/0293922 A1* | 12/2006 | Seare | G06Q 10/00 705/2 |
| 2007/0078680 A1* | 4/2007 | Wennberg | G16H 40/20 705/2 |
| 2007/0106533 A1 | 5/2007 | Greene | |
| 2008/0091466 A1* | 4/2008 | Butler | G16H 40/67 705/2 |
| 2008/0288286 A1* | 11/2008 | Noreen | G06Q 10/06 705/2 |
| 2009/0033664 A1 | 2/2009 | Hao et al. | |

OTHER PUBLICATIONS

T. Stukel et al., Analysis of Observational Studies in the Presence of Treatment Selection Bias: Effects of Invasive Cardiac Management on AMI Survival Using Propensity Score and Instrumental Variable Methods, JAMA 297(3), 17 pages, Jan. 17, 2007.

T. Stukel et al., "Long-term Outcomes of Regional Variations in Intensity of Invasive vs Medical Management of Medicare Patients With Acute Myocardial Infarction," JAMA 293 (11), pp. 1329-1337, Mar. 16, 2005.

T. Hofer et al., "The Unreliability of Individual Physician "Report Cards" for Assessing the Costs and Quality of Care of a Chronic Disease," JAMA, vol. 281, No. 22, pp. 2098-2105, Jun. 9, 1999.

S. Bronskill, "Longitudinal profiles of health care providers," Statistics in Medicine, vol. 21, pp. 1067-1088, 2002 (no month).

S. Anderson et al., "The Gatekeeper Effect on Managing Acute Medical Conditions," Medical Interface, pp. 122-129, Sep. 1996.

R. Schneeweiss et al., "Diagnosis Clusters: A New Tool for Analyzing the Content of Ambulatory Medical Care," Medical Care, vol. XXI, No. 1, pp. 105-122, Jan. 1983.

R. Schneeweiss et al., "Diagnosis Clusters Adapted for ICD-9-CM and ICHPPC-2", The Journal of Family Practice, vol. 22, No. 1, pp. 69-72, 1986 (no month).

R. Greene et al., "Increasing Adherence to a Community-Based Guideline for Acute Sinusitis through Education, Physician Profiling, and Financial Incentives," American Journal of Managed Care, vol. 10, No. 10, pp. 670-678, Oct. 2004.

R. Greene et al., "Beyond the Efficiency Index: Finding a Better Way to Reduce Overuse and Increase Efficiency in Physician Care," DataWatch, pp. 250-259, May 20, 2008.

M. Hornbrook et al., "Health Care Episodes: Definition, Measurement, and Use," Medical Care Review, vol. 42, No. 2, pp. 163-218, Fall 1985.

J. Wennberg, "Unwarranted variations in healthcare delivery: implications for academic medical centres," BMJ, vol. 325, pp. 961-964, Oct. 26, 2002.

J. Weinstein, "United States' Trends and Regional Variations in Lumbar Spine Surgery: 1992-2003," Spine vol. 31, No. 23, pp. 2707-2714, Nov. 23, 2006.

J. Thomas et al., "Identifying "Practice Efficiency" Outliers Among Primary Care Physicians: Effects of Risk Adjustment Methodology and Practice Efficiency Metric," Report to the Robert Woods Johnson Foundation Health Care Financing and Organization (HCFO) Program, HFCO Grant # 36874, Blue Cross Blue Shield of Michigan Foundation Grant #243-II/99, 20 pages, Mar. 18, 2003.

J. Chilingerian, "Evaluating physician efficiency in hospitals: A multivariate analysis of best practices," European Journal of Operational Research, pp. 278-574, 1995.

H. Beckman et al., "Current Approaches to Improving the Value of Care: A Physician's Perspective," The Commonwealth Fund, 46 pages, Nov. 2007.

F.L. Lucas et al., "Temporal Trends in the Utilization of Diagnostic Testing and Treatments for Cardiovascular Disease in the United States, 1993-2001," Circulation 113(3), 12 pages, Jan. 24, 2006.

F. Mullan, "Wrestling with Variation: An Interview with Jack Wennberg," Health Affairs—Web exclusive, pp. 73-80, Oct. 7, 2004.

E. Guadagnoli et al., "Variation in the Use of Cardiac Procedures After Acute Myocardial Infarction," NEJM vol. 333, No. 9, pp. 573-578, Aug. 31, 1995.

E. Fisher et al., The Implications of Regional Variations in Medicare Spending. Part 1: The Content, Quality, and Accessibility of Care, Annals of Internal Medicine, 138, 39 pages, 2003.

D. Salkever et al., "Episode-Based Efficiency Comparisons for Physicians and Nurse Practitioners," Medical Care, vol. XX, No. 2, pp. 143-153, Feb. 1982.

(56) References Cited

OTHER PUBLICATIONS

D. Ko et al., "Regional Differences in Process of Care and Outcomes for Older Acute Myocardial Infarction Patients in the United States and Ontario, Canada," Journal of the American Heart Association, Circulation 2007: 115, pp. 196-203, 2007.
D. Cave, et al. "Who Treats Medical Conditions More Cost Efficiently?," Medical Interface, pp. 136-142, May 1994.
D. Cave, "Small-area variations in the treatment of prevalent medical conditions: A comparison of three cities in the Northeast," J Ambulatory Care Manage, 18(3), pp. 42-57, 1995.
D. Cave, "Profiling Physician Practice Patterns Using Diagnostic Episode Clusters," Medical Care, vol. 33, No. 5, pp. 463-486, May 1995.
D. Cave, "Pattern-of-Treatment Differences Among Primary Care Physicians in Alternative Systems of Care," Benefits Quarterly, pp. 6-19, Third Quarter 1994.
D. Cave, "Analyzing the content of physicians' medical practices," J. Ambulatory Care Manage, vol. 17, No. 3, pp. 15-36, Jul. 1994.
D. Cave et al., "Analyzing Patterns-of-Treatment Data to Provide Feedback to Physicians," Medical Interface, pp. 117-128, Jul. 1994.
B. Sirovich, et al., "Discretionary Decision Making by Primary Care Physicians and the Cost of U.S. Health Care," National Institute of Health, 27(3), pp. 813-823, Jun. 24, 2008.

\* cited by examiner

Marketbasket: General Internists  
SOI - Medical Condition: 1 - Low back pain

Aggregate Group: 1  
Correlation Cutoff: 0.05

NOTE: Screenings, vaccinations, and other preventive services may appear in certain medical conditions due to physician practice and coding patterns.

[Correlation Report] [Clear All MedMarkers] [Print]

[Service Category] [Sub-Service Category] [Sub-Service Detail]

Service Detail Correlation Report

| | Corr | Service | Description | Sub-Service Category | Number Services | Services per Episode | Charge per Service | Unique Practitioners | Performing Practitioners |
|---|---|---|---|---|---|---|---|---|---|
| ☐ | 0.49 | 72148 | mri lumbar spine w/o dye | Imaging | 27 | 0.043 | $165 | 93 | 18.3% |
| ☐ | 0.40 | 85025 | complete cbc w/auto diff wbc | Lab | 45 | 0.071 | $9 | 93 | 18.3% |
| ☐ | 0.39 | 80061 | lipid panel | Lab | 54 | 0.085 | $13 | 93 | 29.0% |
| ☐ | 0.37 | 99283 | emergency dept visit | Professional Visits | 23 | 0.037 | $104 | 93 | 18.3% |
| ☐ | 0.36 | 84443 | assay thyroid stim hormone | Lab | 12 | 0.019 | $13 | 93 | 8.6% |
| ☐ | 0.33 | 80053 | comprehen metabolic panel | Lab | 47 | 0.074 | $11 | 93 | 26.9% |
| ☐ | 0.28 | 81000 | urinalysis, nonauto w/scope | Lab | 70 | 0.110 | $4 | 93 | 31.2% |
| ☐ | 0.25 | 71020 | chest x-ray | Imaging | 19 | 0.030 | $28 | 93 | 11.8% |
| ☐ | 0.23 | 99213 | office/outpatient visit, est 15 | Professional Visits | 505 | 0.813 | $52 | 93 | 96.8% |
| ☐ | 0.23 | 72110 | x-ray exam of lower spine | Imaging | 73 | 0.115 | $32 | 93 | 36.6% |
| ☐ | 0.22 | 72070 | x-ray exam of thoratic spine | Imaging | 13 | 0.021 | $21 | 93 | 6.5% |
| ☐ | 0.22 | 99243 | office consultation 40 | Professional Visits | 8 | 0.013 | $135 | 93 | 4.3% |
| ☐ | 0.21 | 97014 | electric stimulation therapy | Physical Therapy | 14 | 0.023 | $11 | 93 | 6.5% |

FIG. 3

MedMarker Checkout Report                                                                  Print

| Corr | Service | Service or Sub - Service Category | Description | Number Services | Services per Episode | Charge per Service | Unique Practitioners | Performing Practitioners |
|------|---------|-----------------------------------|-------------|-----------------|----------------------|--------------------|-----------------------|--------------------------|
| 0.49 | 72148   | Imaging                           | mri lumbar spine w/o dye | 27 | 0.043 | $165 | 93 | 18.3% |
| 0.23 | 72110   | Imaging                           | x-ray exam of lower spine | 73 | 0.115 | $32 | 93 | 36.6% |
| 0.23 | 99213   | Professional Visits               | office/outpatient visit, est 15 | 505 | 0.813 | $52 | 93 | 96.8% |

FIG. 4

MedMarker Target Report                                                     Export  Print

| Practitioner ID | Practitioner Name | Practitioner Episodes | Efficiency Score * | MedMarkers Meeting Criteria |
|-----------------|-------------------|-----------------------|---------------------|------------------------------|
| 9ETEX1666PVXEB5 | | 7 | 3.29 | 2/3 |
| G2EWNZ666PZIZEN | | 15 | 3.19 | 2/3 |
| 1YI3XM666PV0496 | | 5 | 2.23 | 2/3 |
| G2ENAX666PVOAMX | | 9 | 2.22 | 3/3 |
| G2JRUS666PROORP | | 6 | 2.18 | 1/3 |
| G2BEYN666PRSATZ | | 10 | 2.10 | 1/3 |
| 1MBL19656P1R3NF | | 7 | 2.10 | 3/3 |
| G2BEYN666PRHVWE | | 8 | 1.70 | 3/3 |

Find Practitioners who have at least [1] out of [3] MedMarkers above with

Services per Episode at least [10%] [greater] than the Peer Group Rate

FIG. 5

Practitioner Efficiency Report

*Practitioner Name:*
*Specialty Type :* Dermatologist
*Practitioner ID:*
*Agg Group Name:*

*Quartile:* 4
*Decile:* 10

→ *Efficiency Score:* 1.42
*Significant Difference:* Yes ($P<0.25$)

*Marketbasket:* DERMATOLOGY

*Average Charge Per Episode of Care*

| Medical Condition Name | SOI | Episode Count | Average Charge per Episode | Professional Outpt and Ambulatory | | | | | Facility | | | |
|---|---|---|---|---|---|---|---|---|---|---|---|---|
| | | | | Prof Visits | Diag Tests | Lab/ Path | Med/ Surg | Rx | Prof Inpt | Outpt | Hosp Inpt | Altern Sites | Other Med |
| Peer Group Weighted Avg | — | 33057 | $399 | $83 | $4 | $3 | $103 | $156 | $0 | $7 | $0 | $0 | $7 |
| Practitioner Weighted Avg | — | 174 | *$567 | *$115 | $4 | *$84 | *$132 | *$223 | $0 | *$5 | $0 | $0 | $5 |
| Acne | | | | | | | | | | | | | |
| Peer Group | 1 | 3100 | $265 | $88 | $1 | $7 | $14 | $152 | $0 | $0 | $0 | $0 | $2 |
| Practitioner | 1 | 18 | *$470 | *$131 | $0 | *$49 | *$4 | *$286 | $0 | $0 | $0 | $0 | $0 |
| Benign neoplasm of skin | | | | | | | | | | | | | |
| Peer Group | 1 | 8367 | $279 | $65 | $1 | $76 | $90 | $45 | $0 | $1 | $0 | $0 | $2 |
| Practitioner | 1 | 46 | *$776 | $84 | $21 | *$301 | *$286 | *$84 | $0 | $0 | $0 | *$1 | $19 |
| Dermatitis and eczema | | | | | | | | | | | | | |
| Peer Group | 1 | 3983 | $207 | $82 | $14 | $10 | $21 | $77 | $0 | $0 | $0 | $0 | $3 |
| Practitioner | 1 | 23 | *$385 | *$149 | $14 | $35 | $17 | *$171 | $0 | $0 | $0 | $0 | $0 |

What service category and CPT-4 codes are most correlated to Efficiency Score?

FIG. 6

Services Prevalence Report

*Practitioner Name:*
*Specialty Type:* Dermatologist
*Practitioner ID:*
*Agg Group Name:*

*Quartile:* 4
*Decile:* 10
*Efficiency Score:* 1.42
*Significant Difference:* Yes
(P<0.25)

*Marketbasket:* DERMATOLOGY
*Medical Condition:* All
*SOI:* All
*Sub-Service Category:* 8 Surgical

| | | Practitioner | | | | Peer Group | | | |
|---|---|---|---|---|---|---|---|---|---|
| | Unique Episodes | 174 | | | | 33057 | | | |
| | Unique Practitioner | 1 | | | | 111 | | | |
| Service | Description | Number Services | Services per Episode | Charge per Service | Number Services | Services per Episode | Charge per Service | Services per Episode Percent Difference From Peer Group |
| 11101 | biopsy, skin add on | 110 | 0.609 | $41.90 | 2189 | 0.066 | $31.08 | 854.7% |
| 11100 | biopsy, skin lesion | 83 | 0.477 | $82.36 | 5796 | 0.175 | $71.26 | 172.1% |
| 11402 | exc tr-ext b9+marg 1.1-2 cm | 35 | 0.201 | $132.60 | 407 | 0.012 | $104.52 | 1533.8% |
| 17003 | destruct prematg les, 2 -14 | 18 | 0.103 | $16.22 | 21033 | 0.636 | $10.31 | -83.7% |

Score = 2.73

Correlate to Efficiency Score

| | CPT 11100 | | |
|---|---|---|---|
| ProvID | Eff Score | CPT Score |
| Derm1 | 1.42 | 2.73 |
| Derm2 | 0.92 | 0.80 |
| Derm3 | 1.10 | 1.05 |
| ... | ... | ... |

FIG. 7

Procedure Code Report
Dermatology

| Medical Condition: | All |
| SOI: | All |
| Sub-Service Category: | 8-Surgical |

| Correlation | Procedure | Short Name | Count | Avg Rate per Episode | Avg Cost per Proc |
|---|---|---|---|---|---|
| -0.071 | 17000 | destruct premalg lesion | 11,055 | 0.33 | $52.99 |
| 0.289 | 11100 | biopsy, skin lesion | 5,845 | 0.18 | $71.21 |
| 0.218 | 11101 | biopsy, skin add-on | 1,718 | 0.05 | $39.48 |
| -0.133 | 11900 | injection into skin lesions | 1,344 | 0.04 | $39.82 |
| 0.053 | 11301 | shave skin lesion | 1,012 | 0.03 | $58.62 |
| 0.039 | 11300 | shave skin lesion | 905 | 0.03 | $38.58 |
| -0.148 | 11901 | added skin lesions injection | 579 | 0.02 | $51.30 |
| 0.302 | 11401 | exc tr- extb9+marg 0.6-1 cm | 528 | 0.02 | $94.38 |
| 0.026 | 96900 | ultraviolet light therapy | 528 | 0.02 | $10.57 |
| 0.051 | 11310 | shave skin lesion | 467 | 0.01 | $52.79 |
| 0.221 | 11402 | exc tr- extb9+marg 1.1-2 cm | 402 | 0.01 | $105.46 |
| 0.059 | 17004 | destroy premlg lesions 15+ | 346 | 0.01 | $185.03 |
| 0.085 | 11305 | shave skin lesion | 275 | 0.01 | $40.27 |
| 0.093 | 11400 | exc tr- ext b9+marg 0.5 < cm | 241 | 0.01 | $84.80 |

Number of Physicians = 111

MedMarker:
Build a procedure group around
Skin Biopsies
PG=11100 - 11101

FIG. 8

SYSTEM, METHOD, AND GRAPHICAL USER INTERFACE FOR IDENTIFYING MEDICAL CARE PROVIDERS OUTSIDE A PROCESS-OF-CARE STANDARD

CROSS REFERENCE TO RELATED APPLICATIONS

This application is a continuation of U.S. patent application Ser. No. 17/039,309 filed Sep. 30, 2020, which is a Continuation-in-Part of U.S. patent application Ser. No. 15/162,217 filed May 23, 2016, which is a continuation of U.S. patent application Ser. No. 14/172,728 filed Feb. 4, 2014, which is a Continuation-in-Part of co-pending U.S. patent application Ser. No. 13/621,222 filed Sep. 15, 2012, which is a continuation of U.S. patent application Ser. No. 12/473,147, filed May 27, 2009 and issued as U.S. Pat. No. 8,301,464 on Oct. 30, 2012, which claims priority to our provisional patent application entitled "Method And System For Analyzing Physician Efficiency Scores To Identify Reasons For Inefficient And Efficient Practice Patterns", with application No. 61/082,080, and filed Jul. 18, 2008, all incorporated herein by reference. Moreover, application Ser. No. 14/172,728, of which this application is a Continuation-in-Part of a continuation as stated above, also claims priority to our provisional patent application entitled "Method And System For Analyzing Physician Efficiency Scores To Identify Reasons For Inefficient And Efficient Practice Patterns", with application No. 61/867,577, filed Aug. 19, 2013, all incorporated herein by reference. Moreover application Ser. No. 14/172,728, of which this application is a Continuation-in-Part of a continuation as stated above, also is a continuation of co-pending U.S. patent application Ser. No. 13/970,564, filed Aug. 19, 2013, which is a continuation-in-part of co-pending U.S. patent application Ser. No. 13/621,222 filed Sep. 15, 2012, all incorporated herein by reference.

FIELD

The present disclosure generally relates to analyzing health care information and, more specifically, to a computer-implemented tool for presenting a compact, concise, and understandable analysis of medical care information for evaluating medical care providers against process-of-care standards.

BACKGROUND

Health care costs continue to rise at a rapid rate and total national health expenditures are expected to rise at twice the rate of inflation in 2008. U.S. health care spending is expected to increase at similar levels for the next decade.

One factor contributing to rising health care costs is due to 10% to 20% of physicians, across specialty types, practicing inefficiently. Efficiency means using an appropriate amount of medical resources in an appropriate setting to treat a medical condition or given number of medical conditions, and achieving a desired health outcome and quality of patient care. Thus, efficiency is a function of unit price, volume of service, intensity of service, and quality of service. The inefficient practitioners are often those 10% to 20% of practitioners by specialty type utilizing significantly more services to treat a given grouping of patients with equivalent medical conditions or condition-specific episodes of care as compared to their immediate peer group or best practice guideline. The inefficient practitioners can be responsible for driving 10% to 20% of the unnecessary, excess, medical expenditures incurred by employers and other health care purchasers, equating to billions of dollars nationally.

Currently health plans, insurance companies, third party administrators (TPAs), health maintenance organizations, and other health firms (which collectively shall be called "health plans") expend a significant amount of technical, clinical, and analytical resources trying to identify the inefficient practitioners.

Once health plans have identified inefficient practitioner, they realize that each practitioner has a different practice pattern to deal with and has its own little 'microcosm' of practice. At the microcosm level, many clinical and analytical resources are currently expended trying to determine the microcosm practice patterns for each practitioner for each specialty type. The result is that health plans may end up managing hundreds of different practice patterns which is time and resource intensive and makes monitoring over time difficult.

It is often extremely difficult and costly to identify and target the one or two services most associated with practitioner efficiency. Different practice patterns of each practitioner, as well as the inability to easily identify services most associated with practitioner efficiency, make it challenging and costly for health plans to embark on strategies to reduce expenditure and improve quality. Programs such as targeted practitioner education and behavioral change, Pay for Performance (P4P) and value-based benefit plan design become more resource intensive and costly and less effective due to difficulties in knowing where to focus and areas to target for improvements. Additionally, the lack of focus results in challenges in monitoring and measuring improvements over time.

Known computer-implemented systems are available to analyze the information in a typical claim line item (CLI) file, which may contain tens of thousands, hundreds of thousands, or millions of claim line item records, each record corresponding to a procedure or service for which a claim was submitted to a health plan. However, these known computer-implemented systems lack the functionality to guide decision-makers for healthcare provider organizations (e.g., groups of individual medical care providers practicing in a given office network, hospital group, or other healthcare provider system) and/or health plans through a tiered analysis and distillation of the claim line item information that provides objective indications of the patterns of practice most suitably targeted for process-of-care improvement, both in general (e.g., across all medical care providers in a plan) and specifically (for particular medical care providers). Moreover, these known computer-implemented systems lack the functionality to guide such decision-makers in the selection, understanding, and application of meaningful thresholds for more complex evaluations for medical care providers.

One non-limiting example of the need for a tool to guide decision-makers in more complex evaluations arises in the context of prior authorization requirements. Health plans often require that medical care providers request prior authorization for certain procedures or services, so that the health plan may confirm that the procedure or service is indicated for the applicable medical condition and severity. Prior authorization requirements impose administrative burdens on both healthcare provider organizations and health plans. However, known computer-implemented healthcare analysis systems provide no objective guidance to decision-makers to assist in determining when prior authorization requirements may be relaxed for a particular healthcare provider organization, or for particular medical specialty groups (e.g., cardiology or orthopedics) within a particular healthcare provider organization. Due to the lack of assistance in establishing an objective standard, conventional computer-implemented healthcare analysis systems likewise provide no objective guidance to the healthcare provider organization as to what performance goals must be achieved in order to obtain relaxation of prior authorization requirements.

BRIEF DESCRIPTION

In one aspect, a computer system for identifying medical care providers outside a process-of-care standard for a field of health care is provided. The computer system includes at least one processor and a memory coupled to the processor containing computer executable instructions that, when executed, cause the at least one processor to perform steps that include retrieving claim line item information including at least 1,000 claim line item records for episodes of care attributable to a first medical care provider. The claim line item information includes, in aggregate, at least 40 codes each used to report a corresponding one of a medical, surgical, or diagnostic procedure or service. The steps also include retrieving, from a database, definitions for marker code groups associated with each medical condition of a set of medical conditions. Each of the marker code groups includes one or more related codes from among the at least 40 codes, and each marker code group and the associated medical condition defines a marker-condition pair. The steps further include deriving, for each marker-condition pair for the set of medical conditions, an actual rate of utilization of the marker code group for episodes of the associated medical condition in the claim line item information, and assigning a status to each marker-condition pair for the set of medical conditions. The status is selected from among a group comprising (i) a fail status, assigned in response to the actual rate of utilization exceeding a target rate of utilization of the marker code group for episodes of the associated medical condition, and (ii) a pass status, assigned in response to the actual rate of utilization not exceeding the target rate of utilization. Additionally, the steps include aggregating the statuses across the marker-condition pairs of the set of medical conditions to obtain an overall score for the first medical care provider, and causing an output to be displayed in a viewable format. The output includes the overall score, each marker-condition pair of the set of medical conditions, and the status for each marker-condition pair of the set of medical conditions.

In another aspect, a method, implemented on a computer system, of identifying medical care providers outside a process-of-care standard for a field of health care is provided. The computer system includes at least one processor. The method steps, each performed by the at least one processor, include retrieving claim line item information including at least 1,000 claim line item records for episodes of care attributable to a first medical care provider. The claim line item information includes, in aggregate, at least 40 codes each used to report a corresponding one of a medical, surgical, or diagnostic procedure or service. The steps also include retrieving, from a database, definitions for marker code groups associated with each medical condition of a set of medical conditions. Each of the marker code groups includes one or more related codes from among the at least 40 codes, and each marker code group and the associated medical condition defines a marker-condition pair. The steps further include deriving, for each marker-condition pair for the set of medical conditions, an actual rate of utilization of the marker code group for episodes of the associated medical condition in the claim line item information, and assigning a status to each marker-condition pair for the set of medical conditions. The status is selected from among a group comprising (i) a fail status, assigned in response to the actual rate of utilization exceeding a target rate of utilization of the marker code group for episodes of the associated medical condition, and (ii) a pass status, assigned in response to the actual rate of utilization not exceeding the target rate of utilization. Additionally, the steps include aggregating the statuses across the marker-condition pairs of the set of medical conditions to obtain an overall score for the first medical care provider, and causing an output to be displayed in a viewable format. The output includes the overall score, each marker-condition pair of the set of medical conditions, and the status for each marker-condition pair of the set of medical conditions.

In another aspect, a non-transitory computer-readable medium containing computer instructions for identifying medical care providers outside a process-of-care standard for a field of health care is provided. When executed by a processor, the computer instructions cause the processor to perform steps that include retrieving claim line item information including at least 1,000 claim line item records for episodes of care attributable to a first medical care provider. The claim line item information includes, in aggregate, at least 40 codes each used to report a corresponding one of a medical, surgical, or diagnostic procedure or service. The steps also include retrieving, from a database, definitions for marker code groups associated with each medical condition of a set of medical conditions. Each of the marker code groups includes one or more related codes from among the at least 40 codes, and each marker code group and the associated medical condition defines a marker-condition pair. The steps further include deriving, for each marker-condition pair for the set of medical conditions, an actual rate of utilization of the marker code group for episodes of the associated medical condition in the claim line item information, and assigning a status to each marker-condition pair for the set of medical conditions. The status is selected from among a group comprising (i) a fail status, assigned in response to the actual rate of utilization exceeding a target rate of utilization of the marker code group for episodes of the associated medical condition, and (ii) a pass status, assigned in response to the actual rate of utilization not exceeding the target rate of utilization. Additionally, the steps include aggregating the statuses across the marker-condition pairs of the set of medical conditions to obtain an overall score for the first medical care provider, and causing an output to be displayed in a viewable format. The output includes the overall score, each marker-condition pair of the set of medical conditions, and the status for each marker-condition pair of the set of medical conditions.

In another aspect, a graphical user interface (GUI) for use in evaluating a plurality of medical care providers against process-of-care standards is provided. The GUI is implemented by a processor in communication with a memory device, a user input device, and a display device. The GUI includes a configuration display tier including a specialty control enabling a selection, via the user input device, of a medical specialty from among a plurality of medical specialties. Each of the medical specialties is associated in the memory device with one or more pairs of medical conditions and marker code groups, and each marker code group and the associated medical condition define a marker-condition pair. The configuration display tier also includes a target control enabling a selection, via the user input device, of a target point definition. The GUI also includes a services summary display tier, displayable in response to at least one selection, via the user input device, on the configuration tier display. The services summary display tier includes a listing of the one or more marker-condition pairs associated with the medical specialty selected via the specialty control, and, for each of the listed marker-condition pairs, a target point for a rate of utilization of the marker code group for the associated medical condition. The target point is determined by applying, by the processor for each of the listed pairs, the target point definition to a protocol range associated with the pair in the memory device. The GUI further includes a service detail display tier displayable in response to a selection, via the user input device, of one of the listed marker-condition pairs on the services summary display tier. The service detail display tier includes a listing of qualifying medical care providers of the plurality of medical care providers. The qualifying medical care providers meet a qualifying standard for analysis with respect to the selected pair. The service detail display tier also includes, for each of the listed qualifying medical care providers, an indication of an amount of excess usage of the marker code group of the selected pair with respect to episodes of the medical condition of the selected pair. The amount of the excess usage is determined, by the processor, by (i) parsing claim line item information stored in the memory device to determine an actual rate of utilization of the marker code group in episodes of the medical condition attributed to the respective listed qualifying medical care provider, and (ii) comparing the target point for the selected pair to the actual rate of utilization. The service detail display tier also includes, for each of the listed qualifying medical care providers, an estimated monetary savings realizable in response to a reduction of the actual rate of utilization to match the target point.

In another aspect, a graphical user interface (GUI) for use in evaluating a plurality of medical care providers against process-of-care standards is provided. The GUI is implemented by a processor in communication with a memory device, a user input device, and a display device. The GUI includes a configuration display tier including a specialty control enabling a selection, via the user input device, of a medical specialty from among a plurality of medical specialties. Each of the medical specialties is associated in the memory device with one or more pairs of medical conditions and marker code groups, and each marker code group and the associated medical condition define a marker-condition pair. The configuration display tier also includes a target control enabling a selection, via the user input device, of a target point definition. The GUI also includes a providers summary display tier, displayable in response to at least one selection, via the user input device, on the configuration tier display. The providers summary display tier includes a listing of the medical care providers meeting a qualifying standard for at least one pair of the one or more marker-condition pairs associated with the medical specialty selected via the specialty control, and an overall score for each of the listed medical care providers. The overall score is determined by parsing, by the processor for each at least one qualifying marker-condition pair, claim line item information stored in the memory device to determine an actual rate of utilization of the marker code group of the pair by the listed medical care provider for episodes of the medical condition of the pair; comparing, by the processor for each at least one qualifying pair, the actual rate of utilization to a target point for a rate of utilization of the marker code group for the associated medical condition, wherein the target point is determined by applying, by the processor, the target point definition to a protocol range associated with the respective pair in the memory device; and aggregating, by the processor, the comparisons to determine the overall score for the respective listed medical care provider. The GUI further includes a provider detail display tier displayable in response to a selection, via the user input device, of one of the listed medical care providers on the providers summary display tier. The provider detail display tier includes a listing of each of the at least one qualifying marker-condition pair for the selected medical care provider, and, for each listed pair, an indication of the comparison of the actual rate of utilization to the target point.

BRIEF DESCRIPTION OF THE DRAWINGS

FIG. 3 is an exemplary Sub-Service Detail Correlation Report, in accordance with one embodiment of the present disclosure;

FIG. 4 shows an exemplary MedMarker Checkout Report, in accordance with the embodiment shown in FIG. 3;

FIG. 5 shows a MedMarker Target Report, in accordance with the embodiment shown in FIG. 4;

FIG. 6 is an exemplary Practitioner Efficiency Report, in accordance with one embodiment of the present invention;

FIG. 7 is an exemplary Service Prevalence Report, in accordance with the example shown in FIG. 6;

FIG. 8 is an exemplary Procedure Code Report for one specialty, in accordance with the disclosure and example shown in FIG. 7;

DETAILED DESCRIPTION

Figure 1:
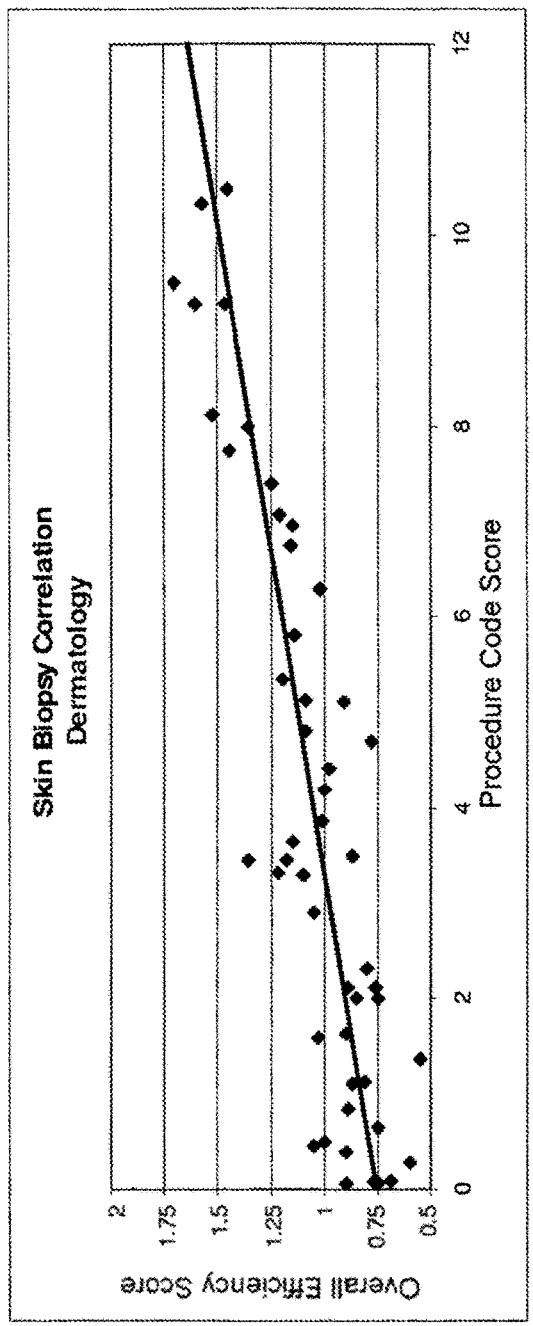
FIG. 1 is a graph showing a Positive Correlation Example.

A Grouper system uses medical care information to build medical condition-specific episodes. Once these condition-specific episodes of care are built, then the episodes are examined through an EfficiencyCare system.

Efficiency means using an appropriate amount of medical resources in an appropriate setting to treat a medical condition or a given number of medical conditions, and achieve a desired quality of patient care. Thus, efficiency is a function of unit price, volume of service, intensity of service, and may include a quality of service component.

Volume refers to the number of services performed to treat a specific medical condition (e.g., an office visit, two laboratory tests, and one prescription drug). Intensity refers to the magnitude of medical care ordered to treat a medical condition (e.g., an x-ray versus a computed tomography scan).

The end result there is typically a score between 0.70 and 1.50. This score reflects the resources a health care provider uses in treating a grouping of patients with medical conditions or condition-specific episodes of care as compared to their immediate peer group or a best practice guideline. If a health care provider receives a score of 0.70, then that health care provider is using 30% fewer resources as compared to the peer group.

The Grouper system generates three primary data sets: Assign.tab data set that assigns episodes of care to health care providers; PatientCLI.tab data set that contains patient claim line items (CLI); and EpMaster.tab data set that contains episodes of care information. The EfficiencyCare system utilizes the Assign.tab data set to generate: a Score.tab data set that includes health care provider efficiency scores; a Detail.tab data set that provides health care provider efficiency score details; and an ProvEp.tab data set that provides health care provider efficiency episodes. The present invention primarily involves a BullsEye system that utilizes those data sets described above to generate a BullsEyeMB.tab and BullsEyeMCID.tab data set that targets medical care information most related to or indicative of health care provider efficiency and inefficiency.

There are three input files to one embodiment of the present invention. One of these input files comes from the Grouper system, and it's called the Patient CLI File 42. This file contains all the claim line items from the CLI Input File, but with the claims organized by medical condition episode of care. In one embodiment, 11 additional pieces of information are added to each claim line item (CLI), and this is the Patient CLI File. These additional pieces of information are added for ease of data mining.

The other two input files for one embodiment of the present invention are output files from EfficiencyCare system. One of these files is the Detail.tab File 68. A record in this file is the health care provider (e.g. physician).

The other file is called the ProvEP.tab File 44, which is an episode file, and it contains all the final episodes of care that made it through EfficiencyCare system and into the Detail.tab file 68. In this embodiment, the ProvEP.tab File 44 is preferred to have because it contains the episode identifiers in this file that allow the present invention to tie back the Claim Line Items (CLIs) in the Patient CLI File.

In one embodiment of the present invention the ProvEP.tab File 44 is used to identify the episode IDs for a health care provider, and it is these episode IDs that are assigned to the health care provider (e.g. physician) and used to calculate his or her efficiency score. Then, the present invention data mines over into the PatientCLI.tab File 42 to find out the CPT-4 codes responsible for a provider's 1.25 or 1.40 efficiency score. That is, determining why the provider is using more or fewer services. However, there are hundreds of potential CPT-4 codes that could be the cause, because a large number of different medical conditions are typically being examined for each health care provider. So, the present invention uses a statistical measure, such as a Pearson's Correlation (a statistic that associates two variables—in this case it is typically the health care provider's efficiency score from EfficiencyCare system (other statistical tools, models, and distributions are also within the scope of this invention)), to a procedure or service (e.g., CPT-4 or HCPCS code) score. The closer to 1.00, the stronger the association (with a Pearson's correlation coefficient). So, the present invention typically reviews large numbers of potential procedure or service (e.g., CPT-4 or HCPCS) codes that could potentially be a primary cause of efficiency or inefficiency, and then determines that a clinical leader should really just focus on a small number (e.g. 2 to 5) of procedure or service codes because these are the procedure or service codes that tend to be most associated with those health care provider's efficiency scores that are high, for example, 1.20 and above, or low. But, also note that these same procedure or service codes identify procedures that efficient providers are doing much less of. Thus, these MedMarkers (i.e., procedures or service codes associated with provider efficiency scores) may also be used to identify efficient health care providers as well. This is why typically MedMarkers are those procedures or services that are associated with provider efficiency scores. And note that health care provider efficiency scoring is preferably done on a specialty by specialty basis, so cardiologists are evaluated separately from general internists and separately from pediatricians.

The present invention "automates" the process for targeting these MedMarkers. That is, analysts at a health plan, physician group, or any other organization might be able to look for these associations by doing a specialized three month study, and then determining the procedures and services (e.g., CPT-4 and HCPCS) associated with the efficiency score of health care providers for a specialty type. This is a long process. The present invention provides software, methods, and algorithms that automate this process, greatly reducing the time needed to find these associations, as well as increasing the accuracy of the results.

After selecting the MedMarkers, the present invention then targets the health care providers that meet the specialty-specific practice pattern as reflected by the MedMarkers selected by a user. It can then present the specified MedMarker results (rates per episode of care) for the health care provider as compared to the selected peer group.

The present invention saves information technology (IT) resources, statistician and analyst resources, and clinical resources needed by a health plan, physician group, or any other organization to identify these important MedMarkers. The process is automated.

Also, once these MedMarkers are known, then the health plan, physician group, or any other organization can take action (i.e., implement strategies that fit each health plan, physician group, or any other organization's philosophies for reducing practice patterns variation) to improve efficiency through working with the health care providers to reduce variability in the identified MedMarkers, focus health care payment reform with respect to the MedMarkers, and implement health plan benefit plan design changes such as adding in deductibles or copayments for the MedMarkers to make the consumer more aware of those services (i.e., MedMarkers) associated with inefficient health care provider practice patterns.

The following personnel in a health plan or physician group can use these MedMarkers to improve medical management performance: medical directors to work with network health care providers to improve performance; health care analysts and informatics specialists that examine claims data to observe reasons for health care provider practice pattern differences or variation; health care actuaries that want to understand services and procedures (i.e., MedMarkers) to target to change health care provider reimbursement to reduce adverse incentives for health care providers to perform more of a certain service or procedure.

One embodiment of the present invention utilizes ASCII tab-delimited database output files from the Grouper system and the EfficiencyCare system. There are the Detail.tab 68, PatientCLI.tab 42, and ProvEP.tab 44 Files. Then, this embodiment, using these input files, produces two intermediate output files, ProvCLI.tab and MinProvEp.tab. These intermediate output files are then used to produce two final output files, BullsEyeMB.tab and BullsEyeMCID.tab. Other file and data structures are also within the scope of the present invention, including databases.

The present invention is the first to use statistical techniques that automates the process for identifying only those procedures and services (e.g., CPT-4 and HCPCS codes) that are most associated with the health care provider efficiency score. One of the unexpected advantages is that the MedMarkers are often unexpected, and sometimes even counterintuitive.

Also, in other embodiments of the present invention:

In the preferred embodiment, only services and procedures are analyzed. However, in another embodiment, drug prescriptions are analyzed in a similar manner.

In another embodiment, there may be a spreadsheet that loads the user identified MedMarkers, the MedMarker service rate per episode, the targeted lower MedMarker rate per episode, the average allowed charge amount for each MedMarker, and the prevalence rate of the medical condition. The spreadsheet can then calculate potential savings for the user using the below formula:

Savings Calculation=Current MedMarker services per episode(−)Target MedMarker services per episode(x)Average allowed charge per service (x)Number of episodes In another embodiment, Service Code Groups are built. In one example, two unique CPT-4 codes for skin biopsy (11100 and 11101) may be examined separately, and therefore, perform a Pearson's correlation on them separately. But, in another embodiment, they are combined together into a specific Service Code Group, which is this case can be called Skin Biopsies=11100+11101. The rates per episode would also be combined and the present invention would be run only after Service Code Groups are formed to find MedMarkers. Here are some possible Service Code Groups:

Destruction of Premalignant Lesions=17000+17004 (these are two of several CPT-4 codes corresponding to Destruction of Premalignant Lesions)

Shave Skin Lesions=11300+11301+11305+11310 (these are some of the several CPT-4 codes corresponding to Shave Skin Lesions)

Calculating the Pearson's Correlations, eventually, on Service Code Groups in some situations may result in more meaningful results to a user than just inspecting each CPT-4 code result individually. Note that the CPT-4 codes in a Service Code Group often look very similar in terms of their verbal description—because they are. For example, under the Destruction of Premalignant Lesions, it may be that code 17000 is used for destroying fewer than 15 lesions, and code 17004 is used for billing purposes for destroying more than 15 lesions. One can see on the verbal description for the codes that code 17004 has +15 lesions on it. Thus, these codes are very similar, and sometimes are just volume oriented. Here's another potential Service Code Group:

Upper Gastrointestinal (GI) Endoscopy=43239+43235 (these are two of several CPT-4 codes corresponding to Upper GI Endoscopy), whereby:
43239=Upper GI Endoscopy with biopsy
43239=Upper GI Endoscopy, diagnosis without biopsy Thus, here, the determination is not made based on numbers, but instead a moderate procedure type difference which is having a biopsy present or not. However, this still would potentially be a good Service Code Group.

One embodiment of the present invention is made up of four components:

The Grouper system groups unique ICD.9 diagnosis codes into 526 meaningful medical conditions based on clinical homogeneity with respect to generating a similar clinical response from health care providers treating a patient.

The EfficiencyCare system is health care provider efficiency measurement software that takes the output from the Grouper system and develops specialty-specific health care provider efficiency scores that compare individual health care provider efficiency against the efficiency of a peer group of interest or practice pattern of interest.

Correlation Calculation Software takes output from the Grouper system and EfficiencyCare system and performs correlation analysis of health care providers' service, sub-service, and procedure or service code scores as compared to their efficiency score.

A Reporting Dashboard, Other Reports, and Open Architecture Output Files. The Reporting Dashboard produces correlation summary reports by service category, sub-service category, and procedures and service code. Reports may include a MedMarker Selection/Summary Report, and Health Care Provider Summary Report. Embodiments of the present invention also provides other reports at key points during processing. All reports are based on output files accessible to the user, and these output files may be used for additional client-developed analysis.

There are several ways that the present invention may be used to add value to an organization. The present invention rapidly targets MedMarkers (i.e., those few procedures and services most associated with health care provider efficiency scores). Knowing these MedMarkers, the present invention identifies health care providers meeting an organization's established MedMarker criteria. On drill-down, the user generally knows the established MedMarker practice patterns per identified health care provider.

Next, users can identify a practice pattern (preferably per specialty type) that identifies inefficient health care providers. Therefore, they may develop and educate their medical management staff on a standard, MedMarker-based, practice pattern. This enables an organization's medical management staff to cost-effectively implement and monitor one standard health care provider feedback program.

Moreover, MedMarkers identified by the present invention identify potential areas of significant procedure and service over-utilization, upcoding, and unbundling. Therefore, MedMarkers may serve as a source for potential health care provider fee payment adjustments by specialty type per region. Here are some examples:

Potential over-utilization example: Dermatologists receiving an inefficient score perform more skin biopsies for the same grouping of medical conditions.

Potential upcoding example: Dermatologists receiving an inefficient score upcode their office visits from 10 minutes to 15-or-20 minutes.

Potential unbundling example: Dermatologists performing a skin biopsy receive payment for both a 20 minute office visit and the skin biopsy, increasing their payment over 300% as compared to a 10 minute office visit alone.

An organization now can have explicit procedures and services to improve its current health care provider payment system by implementing changes to reduce over-utilization, upcoding, and unbundling.

Furthermore, health services research shows that health care provider efficiency measurement methodologies often falsely identify some health care providers as inefficient, when in fact, the health care providers really are efficient ("false positives"). As a result, health care providers may be inappropriately excluded from high performance networks or not receive pay for performance bonuses.

For the first time, organizations can have an automated tool to validate the accuracy of their health care provider efficiency scores. In order for each health care provider's score to be validated as accurate, they can confirm that the health care provider has a higher MedMarker utilization per episode (as compared to the peer group). The end result will typically be higher acceptance of results by network health care providers, thereby reducing potential conflicts, as well as reducing the clinical and analyst resources used to justify the accuracy of each score.

The present invention uses the output from Grouper and EfficiencyCare systems to develop specialty-specific correlations to health care provider efficiency at the:

Service and sub-service category level
Medical condition level
Procedure or service code level, There are several steps to identifying a MedMarker (i.e. a procedure and service correlated to health care provider efficiency scores):

Apply minimum episode criteria for health care providers to be used in correlation analysis.
For each health care provider, calculate an overall weighted average service and sub-service category score.
For each health care provider, create a medical condition-specific service and sub-service category score.
Calculate an overall weighted average procedure or service code score for each health care provider.
Calculate a medical condition-specific procedure or service code score for each health care provider.
If desired, remove outlier health care providers from analysis at a service category, sub-service category, and procedure or service code level.
Calculate the correlation to health care provider efficiency scores at each level described above using a Pearson's correlation calculation.
Correlated service and sub-service categories and procedures or services can be selected as MedMarkers and used to identify health care providers that meet a desired practice pattern.

These steps preferably occur after removing outlier episodes and health care providers that did not meet a minimum episode number established when running EfficiencyCare system. Therefore, outlier episodes identified during efficiency analysis, and health care providers not receiving an efficiency score, are not included in the analysis.

In one embodiment, a health care provider must have a minimum number of non-outlier episodes at the specialty-specific market basket level or medical condition level in order to be included in the correlation analysis. This minimum episode number should not be confused with a minimum episode number used to establish whether a health care provider receives an efficiency score.

In one embodiment, each health care provider's overall weighted average service category utilization per episode is divided by the peer group overall weighted average service category utilization per episode to calculate an overall service category score. Also, each health care provider's overall weighted average sub-service category utilization per episode is divided by the corresponding peer group's overall weighted average sub-service category utilization per episode to calculate an overall sub-service category score.

NOTE: Overall utilization rates for service and sub-service categories may be found in the EfficiencyCare system output file: Detail.tab.

In one embodiment, CPT-4 and HCPCS codes represent the procedure or service code level detail that is used to report services per episode rate for the health care provider and the peer group. The present invention uses this information at the overall weighted average level to calculate a unique procedure or service code score. Each health care provider's procedure or service code per episode rate is divided by the corresponding peer group procedure or service code per episode rate to calculate an overall procedure or service code score. For example, a dermatologist's overall skin biopsy rate per episode may be 0.477 services per episode. The peer group skin biopsy per episode rate is 0.175, resulting in a CPT-4 score for the dermatologist of a 0.477/0.175=2.72.

Similar to the overall weighted average service and sub-service category score, a medical condition-specific service category and sub-service category utilization score are calculated for each health care provider. Each health care provider's condition-specific service category utilization per episode is divided by the peer group service category utilization per episode to calculate a condition-specific service category score. Also, each health care provider's condition-specific sub-service category utilization per episode is divided by the corresponding peer group sub-service category utilization per episode to calculate a condition-specific sub-service category score.

NOTE: Medical condition-specific utilization rates for service and sub-service categories may be found in the EfficiencyCare system output file: Detail.tab.

In one embodiment, CPT-4 and HCPCS code detail may also be available for medical conditions within a market basket of interest. The condition-specific services per episode rate for the health care provider and the peer group may be used to calculate a service code score. For a specific medical condition, each health care provider's service code per episode rate is divided by the corresponding peer group condition-specific service code per episode rate to calculate a score. For example, a dermatologist's benign neoplasm of the skin biopsy rate per episode may be 0.500 services per episode. The peer group benign neoplasm of the skin biopsy rate per episode may be 0.250, resulting in a CPT-4 score for the dermatologist of a 0.500/0.250=2.00.

In the preferred embodiment health care provider outlier analysis is preferably performed after health care providers receive a service category score. The parameter SWITCH_BE_PROVOUTLIER in the run.ini configuration file defines the percent of health care providers that will be removed from correlation analysis in one embodiment of the present invention. Within each specialty marketbasket's service category, a percentage of health care providers with the greatest absolute variance between the health care provider's efficiency score and the service category score are removed from correlation analysis in this embodiment. The health care provider outlier analysis removes health care providers having differences that are far away from a major part of the data. One reason for removing them is that those health care provider outliers in the "difference area" may not be reliable from a statistical sense. Typically, the same health care providers are removed from sub-service category and procedure or service codes within the corresponding service category for both the overall marketbasket level and medical condition level correlation analysis. The health care providers included in the correlation analysis may differ by service category. For example, the health care provider outlier parameter default value may be 10%. Table 1 refers to a General Internist with an overall efficiency score of a 0.90, and demonstrates if this health care provider is to be included in correlation analysis for two separate service categories. In other embodiments, other health care provider outlier analysis methods may be utilized.

TABLE 1

General Internist Physician Outlier Example

| Service Category | Overall Efficiency Score | Service Category Score | Absolute Variance | Include Physician in Correlation Analysis? (includes corresponding sub-service category and procedure or service level correlation analysis) |
|---|---|---|---|---|
| Diagnostic Tests | 0.90 | 2.50 | 1.60 | No. This physician is in the top 10% of physicians with greatest variance |
| Medical/ Surgical | | | | Yes. This physician is not in the top 10% of physicians with the greatest variance |

If the percent of health care providers removed as outliers cannot be achieved, then no health care providers are removed from the peer group in one embodiment of the present invention. For example, if there are 6 Allergists and 10% are to be removed, no health care providers are removed from the Allergist marketbasket for correlation analysis.

Peer group substitution is preferably used for health care providers who have passed the outlier criteria, but have not performed any services in a service category, sub-service category, or for a service code. Health care providers who did not receive a service category, sub-service category, or procedure or service code score because they did not perform those services or procedures will receive a score of a 1.0, which represents the peer group results. For example, if a health care provider did not perform any imaging tests, the health care provider's overall weighted average sub-service category score for imaging would preferably be substituted with a value of 1.0. In other embodiments, other peer group substitution methods may be utilized.

The main statistical analysis performed in one embodiment of the present invention is the Pearson's correlation analysis. Pearson's correlation analysis is used to calculate the correlation of a service category, sub-service category, or procedure or service code to health care provider efficiency score—Pearson's correlation coefficient (r). In the presentation of the correlation results, the correlation coefficient (r) indicates the strength and direction of a linear relationship between the dependant and independent variables, and varies from a low of −1.00 to a high of 1.00. The higher the absolute value of the coefficient, the stronger the relationship between the two variables. In health services research, two variables may be considered fairly correlated if "r" is greater than some limit (e.g., 0.20 or so). Also, two variables may be considered highly correlated if "r" is greater than some limit (e.g., 0.40 or so). Other statistical measurements are also within the scope of the present invention.

Correlation analysis is typically based on the identification of the dependent and independent variables which defines the detailed level for analysis.

Dependent variable. The dependent variable in the correlation model in the preferred embodiment of the present invention is a health care provider's efficiency score. The dependent variable is the health care provider's specialty-specific overall weighted average efficiency score if looking at the overall market basket level. The dependent variable is the health care provider's specialty-specific and medical condition-specific efficiency score if looking at the medical condition level.

Independent variables. There are three (3) types of independent variables that are included in the preferred embodiment of the present invention. These are listed in the following table.

TABLE 2

Potential Independent Variable Types

| Variable Types | Definition |
|---|---|
| Service Category Score | This is the service category score at either the overall marketbasket level or the medical condition-specific level. In one embodiment, there are 11 service categories. |
| Sub-Service Category Score | This is the sub-service category score at either the overall marketbasket level or the medical condition-specific level. In one embodiment, there are 21 sub-service categories. |
| Procedure or Service Code Score | This is a procedure or service code score at the overall marketbasket level or the medical condition-specific level. In one embodiment, the procedure or service code score is based on CPT-4 or HCPCS codes. |

The Pearson's correlation coefficient (r) is used in one embodiment of the present invention to determine the strength of the relationship between the health care provider efficiency score and health care provider service category, sub-service category, and service code score. This coefficient provides a numeric measure of the strength of the linear relationship between these two variables.

Pearson's correlation coefficient (r) ranges from a low of −1.00 to a high of 1.00. Positive correlations mean that the health care provider service category, sub-service category, and service code scores are positively associated with the health care provider efficiency score. That is, if a health care provider does more of the particular service code per episode as compared to the peer group, then the health care provider most often has an efficiency score greater than a 1.00. Vice versa, if a health care provider does less of the particular service code per episode as compared to the peer group, then the health care provider most often has an efficiency score less than a 1.00. Therefore, a positively correlated service code indicates that health care providers performing more of this service code tend to have more inefficient practice patterns as compared to the peer group. Negative correlations mean that the health care provider service category, sub-service category, and service code scores are negatively associated with the health care provider efficiency score. That is, if a health care provider does more of the particular service code per episode as compared to the peer group, then the health care provider most often has an efficiency score less than a 1.00. Vice versa, if a health care provider does less of the particular service code per episode as compared to the peer group, then the health care provider most often has an efficiency score greater than a 1.00. Therefore, a negatively correlated service code indicates that health care providers performing more of this service code tend to have more efficient practice patterns as compared to the peer group. Note that Pearson's correlation coefficient is used in one embodiment of the present invention and is used here as an example of a measure of correlation. Other measures of correlation are also within the scope of the present invention.

TABLE 3

Potential Correlation Intervals in Relation to Efficiency

| Correlation Range | Correlation to Efficiency or Inefficiency |
|---|---|
| >0.40 | High positive correlation to health care provider efficiency scores; the more he does, the more likely the health care provider is to receive an inefficient score. |
| 0.20 to 0.40 | Good positive correlation to health care provider efficiency scores |
| −0.20 to 0.20 | Low to no correlation to health care provider efficiency scores |
| −0.20 to −0.40 | Good negative correlation to health care provider efficiency scores |
| <−0.40 | High negative correlation to health care provider efficiency scores; the more he does, the more likely the health care provider is to receive an efficient score. |

FIG. 1 is a graph showing a Positive Correlation Example. In this FIG., each procedure score for skin biopsies (CPT-4 11100) has been plotted against each dermatologist's overall health care provider efficiency score. When the CPT-4 score is high, the health care provider efficiency score is high. Alternatively, when the CPT-4 score is low, the overall efficiency score is low, resulting in a high Pearson's correlation coefficient of a 0.64. According to Table 3 (above)—Potential Correlation Intervals in Relation to Efficiency, in this population, skin biopsies have a high positive correlation to health care provider efficiency scores, indicating a health care provider doing more of this procedure is more likely to receive an inefficient score.

Figure 2:
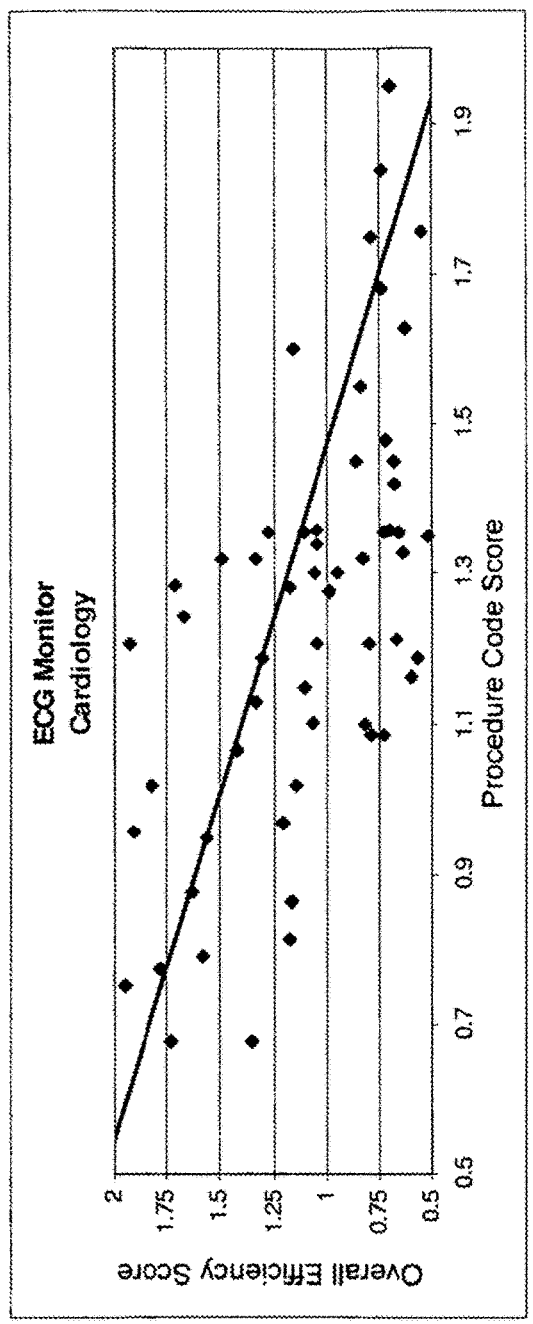
FIG. 2 is a graph showing a Negative Correlation Example.

FIG. 2 is a graph showing a Negative Correlation Example. In this FIG., each procedure score for ECG Monitoring (CPT-4 93325) has been plotted against each Cardiologists' overall health care provider efficiency score. In this example, when the procedure score for ECG Monitoring (CPT-4 93325) for Cardiologists is high, the health care provider efficiency score is low. This is the opposite of the skin biopsy pattern shown above. When the CPT-4 score is low, the overall efficiency score is high, resulting in a negative Pearson's correlation coefficient of a −0.26. According to Table 3 (above)—Potential Correlation Intervals in Relation to Efficiency, in this population, ECG Monitoring has a good negative correlation to health care provider efficiency scores, indicating a health care provider doing more of this procedure is more likely to receive an efficient score.

A MedMarker is preferably a CPT-4 or HCPCS code that is relatively correlated to the health care provider efficiency score. To qualify as a MedMarker, the procedure or service should preferably have the following properties:

Good correlation (using Pearson's correlation "r" in this example) to a health care provider specialty type's overall or medical condition-specific efficiency score;

A higher prevalence rate per overall weighted average episode of care, or medical condition-specific episode of care.

Clinical relevance in terms of medical support literature as to when service should be performed; and A reasonable charge per service (e.g., $50-to-$400 per service in this example). The health care provider's condition-specific efficiency score is a reflection of the services used to treat a specific medical condition as compared to an immediate peer group.

More than a given percentage of the health care providers (within the specialty type of interest) perform one or more of the service code of interest.

The present invention allows an organization to identify one main practice pattern per specialty type per region that is most associated with health care provider efficiency scores, and identify those health care providers who meet this practice pattern.

Identify a MedMarker (or several MedMarkers) that will be used to establish a practice pattern for specialty-specific health care providers in a given region (see FIG. 4). Users can select positively or negatively correlated MedMarkers (see FIG. 1 & FIG. 2).

For the MedMarkers selected, define the percentage above or below the services per episode rate to identify health care providers with a specified practice pattern. For example, for MRI of the lumbar region (CPT-4 72148), a general internist's service per episode rate should be 10% higher than the peer group rate for the health care provider to be defined as meeting the practice pattern (see FIG. 5).

When selecting multiple MedMarkers to establish a practice pattern, a threshold can be set for the amount of MedMarkers that must meet or exceed the services per episode rate. For example, if 7 MedMarkers are used to establish a practice pattern, a user may only require 5 out of 7 MedMarker services per episode rate be met in order to identify a health care provider as matching a specified practice pattern (see FIG. 5).

The present invention will preferably produce a list of Provider IDs that match the identified practice pattern (see FIG. 5). The Provider ID list produced by the present invention can be loaded into EfficiencyCare Practitioner Efficiency Reports to further drill down on their practice patterns.

FIGS. 6 through 8 are diagrams illustrating the process of identifying MedMarkers, in accordance with one embodiment of the present invention. These examples are exemplary, and are only included here for illustrative purposes. It should be understood that these functions are automated in a computer system in a preferred embodiment of the present invention, and the separate reports are shown merely to illustrate the process.

FIG. 6 is an exemplary Practitioner Efficiency Report, in accordance with one embodiment of the present invention. It contains episode information for one practitioner (i.e. health care provider) for a number of medical conditions. For each medical condition, as well as a weighted average of all such medical conditions, averages for a peer group of health care providers are also shown. For each medical condition and weighted average, there are a number of columns. It shows the average charges per episode of care. The first column shows the name of the medical condition. The next shows a Severity of Illness (SOI) level for the condition. This is followed by an episode count and average charger per episode. Then, the average charge per episode is broken down across service categories in columns for: professional visits; diagnostic tests; lab/pathology; medical/surgical; prescriptions (Rx); facility outpatient; facility hospital; alternate sites; and other medical expenses. An efficiency score is computed for the practitioner by dividing his average charge per episode of his average weighted charges by the average charge per episode for the peer group. In this case, the average charge per episode for this practitioner was $567, and for the peer group, it was $399. The quotient of these two average charges is 1.42, which can be utilized as an efficiency measurement. Other methods of and techniques for computing an efficiency measurement or score for health care providers are also within the scope of the present invention. In comparing this health care provider with others, this efficiency rating is in the 4th quartile, or 10th decile. A question is asked, what CPT-4 code is most associated with the efficiency score? There are several steps outlined below to answer this question. The first step is to identify a service category where the health care provider has significantly higher overall weighted average charges than the peer group. In this example, medical/surgical overall weighted average charge for the health care provider is significantly higher than the overall weighted average charge for the peer group as indicated by the asterisk on the practitioner weighted average result for Med/Surg, and is circled to illustrate this.

A next step is to drill-down to the service code level under sub-service ambulatory surgical procedures to identify health care provider service codes with higher per episode rates than the peer group. FIG. 7 is an exemplary Service Prevalence Report in accordance with the example shown in FIG. 6. For the Dermatology specialty the report contains information on services ordered for one healthcare provider and the peer group. The report also shows the number of unique episodes for the healthcare provider and the peer group as well as the number of unique healthcare providers in the peer group. Also, for both the healthcare provider and the peer group, the number of services, number of services per episode, and the charge per service is shown for each service listed. There is also a column showing services per episode percent difference from the peer group.

Next, there is also a CPT-4 table shown in FIG. 7 (in the upper right hand quadrant) for CPT-4 11100. In the CPT-4 11100 table, the overall efficiency scores of several healthcare providers are shown for this CPT-4 code (biopsy, skin lesion). In one embodiment, it would contain entries for each healthcare provider in the peer group having treated a sufficient number of episodes in the Dermatology marketbasket of medical conditions. Also, a CPT-4 score is calculated for this CPT-4 code by dividing a healthcare provider number of services per episode by an average value for his peer group. The CPT-4 score for each healthcare provider in the table is included in a CPT-4 score column along side his efficiency score. In the case of the first Dermatologist in the table, overall efficiency score is 1.42, and the first Dermatologist has a CPT-4 score of 2.73. In one embodiment, this type of CPT-4 table is generated for each CPT-4 code being evaluated as a potential MedMarker. After the CPT-4 table is populated for a CPT-4 code, a statistical measurement, such as a correlation coefficient (e.g. Pearson's "r"), is computed for the pairs of efficiency scores and CPT-4 scores for each row in the table. In one embodiment, a Pearson's coefficient is the statistical measurement calculated. In other embodiments, other measures of correlation or other statistical measurements may be utilized.

Finally, to identify the CPT-4 code most associated with efficiency scores for the Dermatologists, FIG. 8 provides an exemplary Procedure Code Report for the Dermatology specialty type, in accordance with the invention and example shown in FIG. 7. This report shows one line for each CPT-4 code being evaluated as a potential MedMarker for the given sub-service category of ambulatory surgical services. One example is the Pearson's correlation computed for CPT-4 11100 shown in FIG. 7. The first column in the report contains the statistical measurement (e.g. Pearson's correlation coefficient) calculated for pairs of efficiency scores and CPT-4 scores for that CPT-4 code. The second column contains the corresponding CPT-4 procedure code. This is followed by columns for a short name for the CPT-4 code, an average rate per episode for this code, and an average cost per procedure. The CPT-4 codes with sufficiently high positive or negative correlations are considered as MedMarkers. In this FIG. 8, CPT-4 procedure 11100 has a correlation of 0.289, 11101 has a correlation of 0.218, 11401 has a correlation of 0.302, and 11402 has a correlation coefficient of 0.221. These all have a correlation coefficient greater than 0.2, which is a exemplary cutoff in one implementation of the present invention, and these services, therefore, may be considered as potential MedMarkers. They all have a relatively high correlation between efficiency scores and CPT-4 scores. The remainder of the CPT-4 codes listed for this sub-service category have lower correlation coefficients, are thus less correlated, and are preferably eliminated from consideration as potential MedMarkers.

The MedMarker information presented in FIG. 8 is for sub-service category of ambulatory surgical services across all medical conditions in the Dermatology marketbasket. In one embodiment, MedMarkers can be identified across all sub-service category services for a given medical condition (see FIG. 3) FIG. 3 is an exemplary Sub-Service Detail Correlation Report, in accordance with one embodiment of the present invention. This report shows the correlation between different services and health care provider efficiency for a specialty (in this example, General Internist) and a specific medical condition (in this example, Low back pain). The fields in this report are:

| Field Name | Notes |
|---|---|
| | Top of Report |
| Marketbasket | This is the name of the specialty-specific marketbasket selected for analysis. |
| SOI - Medical Condition | A specialty-specific marketbasket consists of the common medical conditions treated by each specialty type. This field presents the medical condition name and the severity-of-illness (SOI) being examined. There are up to three SOI levels for each medical condition, with SOI-1 being the least severe (routine, non-complicated), and SOI-3 being the most severe SOI (severity of illness). |

-continued

| Field Name | Notes |
| --- | --- |
| Aggregate Group | Marketbasket System output contains information organized by aggregate groups that users define. This is the name of the aggregate group relevant to the current data run. |
| Correlation Cutoff | This is the cutoff value used to determine what procedures or services to display on the Sub-Service Detail Report. This parameter is not applicable for the service category and sub-service category level reports. |
| | Body of Report |
| | Columns |
| | This column allows you to select the MedMarkers of interest to add to a user's BullsEye "shopping cart". Any service category or sub-service category row can be selected by checking the box under this column. |
| Corr | This column presents the correlation results of the service categories or sub-service categories to the health care provider's efficiency scores at the overall marketbasket level or the medical condition level within a marketbasket. |
| Service/Sub-Service Category | This column presents the name of the 11 service categories or 21 sub-service categories. |
| Number Services | This column presents the total number of services for the specialty-specific peer group at the overall marketbasket level or the medical condition level within a marketbasket. |
| Service Units | This column presents the type of service associated with each service category or sub-service category. For example, "Professional Visits" service type is office visits. |
| Services per Episode | This column presents the average number of services per episode for the specialty-specific peer group at the overall marketbasket level or the medical condition level. |
| Charge per Service | This column presents the average charge per service for the specialty-specific peer group at the overall marketbasket level or the medical condition level within a marketbasket. |
| Unique Practitioners | This column presents the number of health care providers in the specialty-specific peer group at the overall marketbasket level or the medical condition level within a marketbasket. |
| Performing Practitioners | This column presents the percentage of the health care providers in the peer group having performed the service at least once at the overall marketbasket or the medical condition level. |

As defined earlier in discussion of FIG. 5, FIG. 4 shows an exemplary MedMarker Checkout Report, in accordance with the embodiment shown in FIG. 3. This report is a subset of the report shown in FIG. 3, with columns from that report selected by clicking under the marketbasket icon (※) in the first column.

FIG. 5 shows a MedMarker Target Report, in accordance with the embodiment shown in FIG. 4 as discussed earlier. A user first selects a number of services as show in FIG. 4 by clicking under the marketbasket icon in FIG. 3. The user then selects how many of the marketbasket services are required for a health care provider in this report (the report shown requires one of the three) and a threshold based on the peer group. The report generated lists the practitioners who qualify under these criteria. The fields in this report are:

| Field Name | Notes |
| --- | --- |
| | Top of Report |
| Aggregate Group | Marketbasket System output contains information organized by aggregate groups that you define. This is the name of the aggregate group relevant to the current data run. |
| Marketbasket | This is the name of the specialty-specific marketbasket selected for analysis. |
| Medical Condition | A specialty-specific marketbasket consists of the common medical conditions treated by each health care provider specialty type. This field presents the medical condition name being examined. If analysis is performed at the marketbasket level, this field will contain the value "all". |

-continued

| Field Name | Notes |
| --- | --- |
| SOI | This field presents the severity-of-illness (SOI) being examined. There are up to three SOI levels for each medical condition, with SOL 1 being the least severe (routine, non-complicated), and SOI-3 being the most severe SOI (severity of illness). If analysis is performed at the Marketbasket level, this field will be blank. |
| | Body of Report |
| | Columns |
| Practitioner ID | This is the unique identification number assigned to the health care provider analyzed. |
| Practitioner Name | This is the name of the health care provider analyzed. |
| Efficiency Score | This is the efficiency score for each health care provider. At the marketbasket level, the efficiency score is calculated by dividing the health care provider's weighted average overall charges by the specialty-specific peer group's weighted average overall charges. At the medical condition-SOI level, the efficiency score is calculated by dividing the health care provider's average medical condition-SOI charges by the specialty-specific peer group's average medical condition-SOI charges within a marketbasket. |
| MedMarkers Meeting Criteria | This column presents the number of MedMarker criteria met by each health care provider. |

A Practitioner MedMarker Report (not shown) provides users with additional detailed information for each health care provider displayed in the MedMarker Target Report shown in FIG. 5. The MedMarker Target report has links for each practitioner, and when that link is selected, the details for each of the selected MedMarkers is shown for that practitioners.

Figure 9:
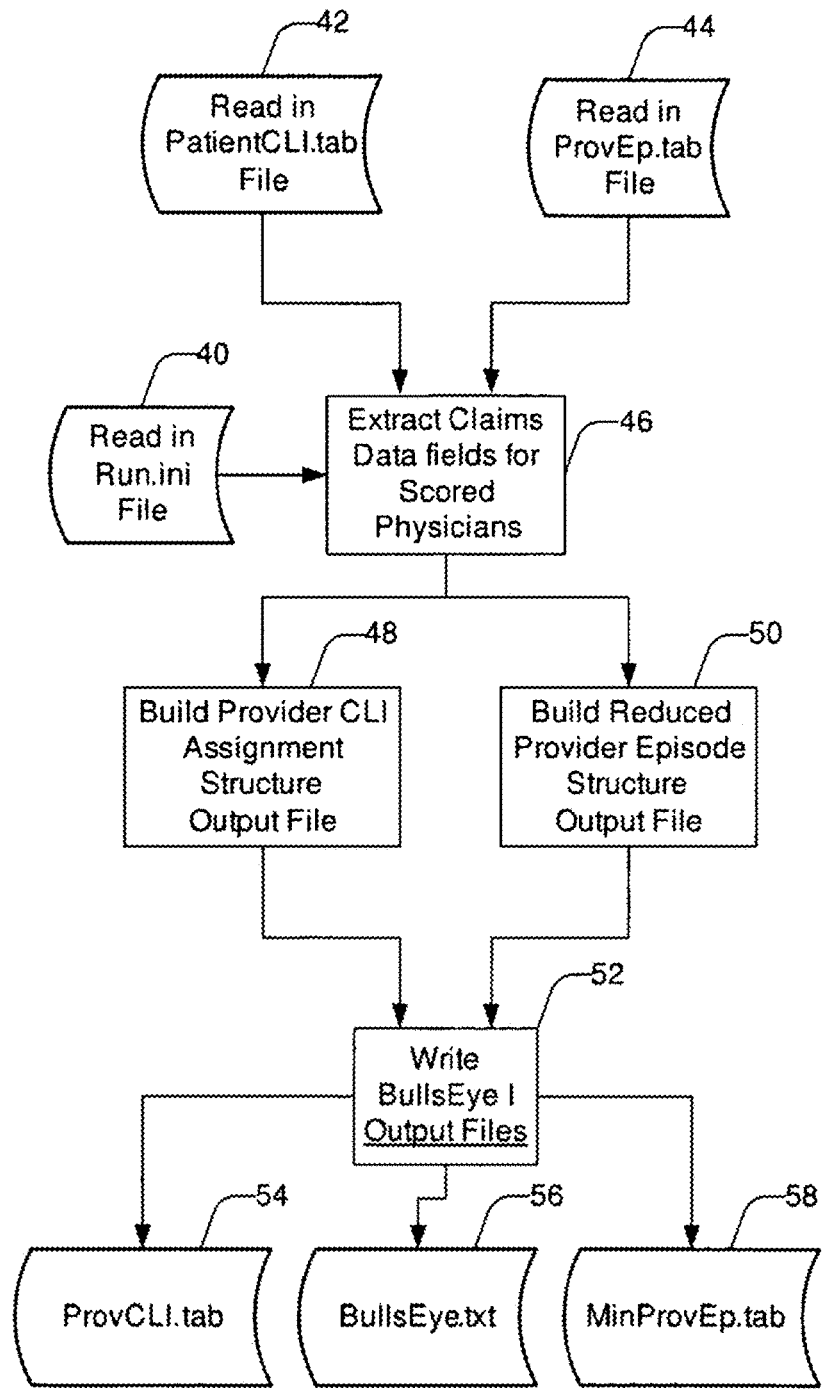
FIGS. 9 and 10 are flowcharts illustrating exemplary operation of one embodiment of the present disclosure.
Figure 10:
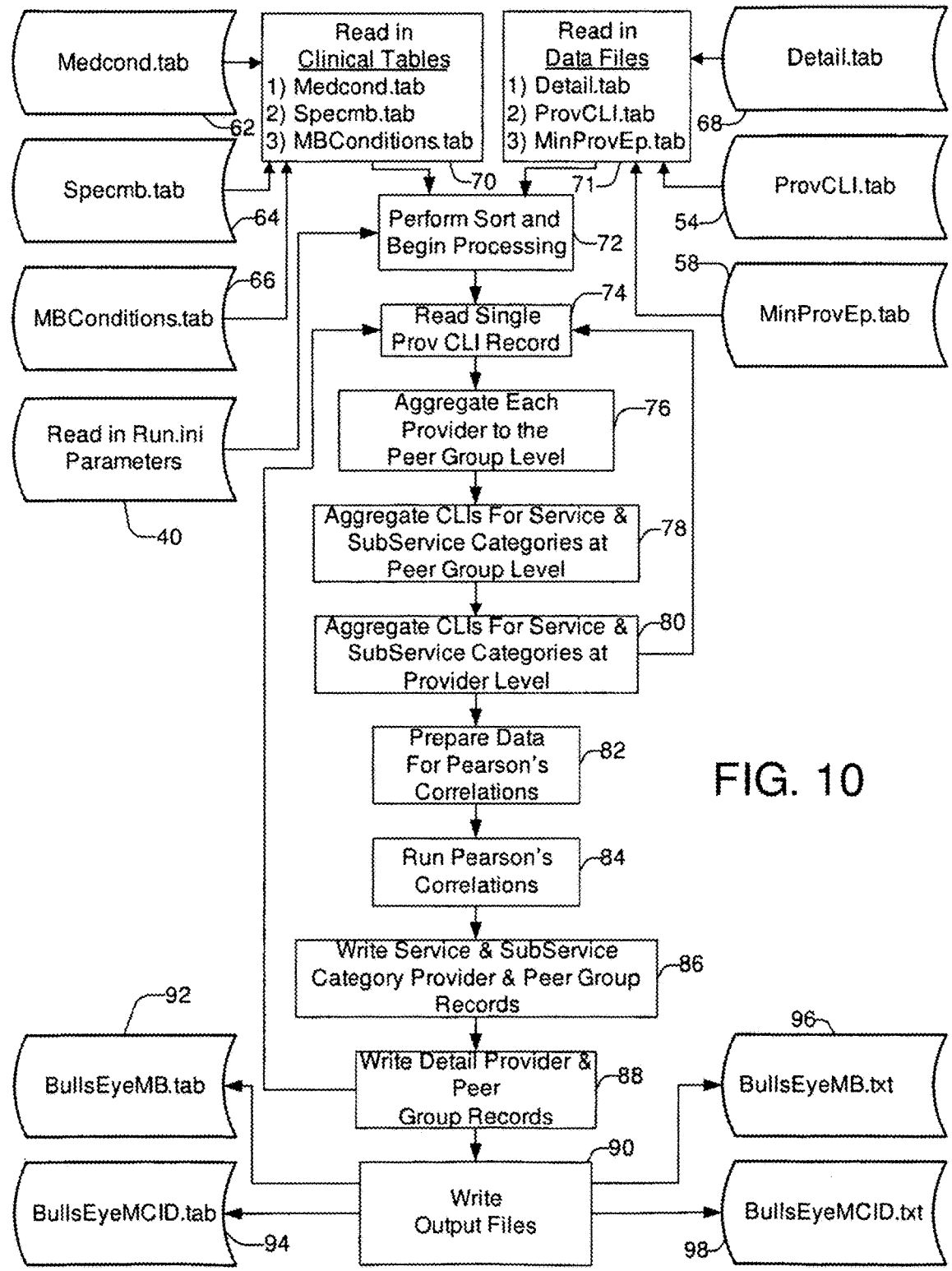

FIGS. 9 and 10 are flowcharts illustrating exemplary operation of one embodiment of the present invention. They are separated into two flowcharts for illustrative purposes, and it should be understood that they may not be separate in different embodiments. Furthermore, files are shown in these flowcharts. It should be understood this is illustrative and that other methods and techniques of data organization and management are also within the scope of the present invention. For example, many of the operations shown may be implemented through database operations in place of file operations.

FIG. 9 starts by reading in a PatientCLI file 42, a ProvEp file 44, and Run.ini parameters 40. From these files, claims data fields are extracted for scored health care providers, step 46. From this, a Provider CLI assignment structure file is built, step 48, and a Reduced Provider Episode Structure Output file is built, step 50. Then, the first phase of files are written, step 50, including a ProvCLI file 54, a BullsEye file 56, and a MinProvEp file 58.

FIG. 10 starts by reading in clinical tables, step 70 from a MedCond file 62, Specmb file 64, and MBConditions file 66. Also, data files are read in, step 68, including: a Detail file 68; the ProvCLI file 54; and the MinProvEp file 58. The Run.ini run time parameters 40 are read in, and a sort is performed, step 72. A loop is entered, starting with reading a single ProvCLI record, step 74. Health care providers are aggregated to the peer group level, step 76. Claim Line Items are aggregated for service and subservice categories at the peer group level, step 78 and at the provider level, step 80. An inner loop repeats for each CLI record, step 74. Then, data is prepared for statistical analysis, step 80, and statistical analysis, such as Pearson's correlation, is performed, step 84. Service and subservice category provider and peer group records are written, step 86, and provider and peer group records are written, step 88. An outer loop then repeats, starting at the beginning of the CLI records, step 74. At the end of the outer loop, the output files are written, step 90, including: a BullsEyeMB.tab file 92; a BullEyeMCID-.tab file 94; a BullsEyeMB.txt file 96; and a BullsEyeM-CID.txt file 98.

Clinical MedMarker Protocol Ranges
Overview

Clinical MedMarker Protocol Ranges are achievable and appropriate ranges of clinical practice for the services and procedures that drive higher cost of care by specialty type (i.e., MedMarker's). The MedMarker services also are process-of-care quality measures that are well-defined by clinical guidelines for many common medical conditions.

The Clinical MedMarker Protocol Ranges foster collaborative discussions between health plans and other payers and the clinical leaders of physician groups and health systems. Such discussions concern what constitutes an achievable and appropriate practice range for a MedMarker. The ranges are based on the objective, collective experience of CCGroup Specialist Panels and a National MedMarker Comparative Database.

Recognizing Value Using Clinical MedMarker Protocol Ranges

Clinical MedMarker Protocol Ranges enable providers and provider groups to improve the quality of care by identifying and reducing unwarranted variations in physician practice patterns, thus slowing the pace of cost increases. The ranges support value-based contracting efforts for both payers and health systems.

From the health plan and payer perspective, they can be used to:
  Negotiate performance-based contracts for fee increases, shared savings, and other value-based reimbursement or risk-sharing programs.
  Communicate to employers the cost-benefit of using providers and groups within the clinically accepted protocol ranges.
  Reduce costs and resources associated with preauthorization programs for provider groups who stay within the Clinical MedMarker Protocol Range.

From the health system or provider group perspective they help:
  Achieve more favorable reimbursement and increase patient volumes by staying within the established, achievable Clinical MedMarker Protocol Ranges.
  Improve the quality of care and reduce unwarranted practice variations through more effective collaboration with payers.

Clinical MedMarker Protocol Range Methodology
Overview

Clinical MedMarker Protocol Ranges leverage two interlocking data sources to create acceptable clinical protocol ranges for many of the most common medical specialties, procedures, and diagnostic tests. The two components are:
  National MedMarker Comparative Database: A national comparison of condition-specific MedMarker utilization rates.
  National Specialist Panels: Nationwide panels of physicians by specialty type; each specialty-specific panel is asked to review the national condition-specific MedMarker utilization to provide their expert opinion on appropriate levels of practice.

Definitions and Concepts

Clinical MedMarker Protocol Range: An achievable range for physician practice based on specialty-specific clinical input. The achievable range applies to ordering or performing specific procedures or diagnostic tests for prevalent and commonly treated medical conditions.

MedMarker: A CPT-4 or HCPCS code or set of codes that is/are highly correlated to the physician-efficiency score in treating a specific medical condition. To qualify as a MedMarker, the procedure or service should preferably have the following properties:
  Good correlation (e.g. using Pearson's "r" correlation) to a physician specialty type's overall or medical condition-specific efficiency score.
  A higher prevalence rate per overall weighted average episode of care or medical condition-specific episode of care.
  Clinical relevance in terms of medical support literature as to when the service should be performed.
  A reasonable charge per service, in a prespecified (e.g. $50-to-$400) range.
  More than a specified (e.g. 30%) of the physicians within the specialty order or perform one or more of the services of interest.

MedMarker correlations: A MedMarker can have positive or negative correlation to physician-efficiency scores. A positively correlated MedMarker of greater than 0.20 is typically a procedure or service that has good-to-high correlation to physician efficiency scores, indicating a physician doing more of the procedure is more likely to receive an efficient score, while a negatively correlated. MedMarker is typically a procedure or service that has good-to-high correlation to physician efficiency scores, indicating a physician doing more of the procedure is more likely to receive an inefficient score.

Episodes of care: All the diagnostic and therapeutic services (e.g., ambulatory, outpatient, inpatient, facility, and prescription drugs) used to treat an individual's specific medical condition across a contiguous length of time (see episode duration) during which an individual seeks care for that specific medical condition.

Episode duration: The length of time, in number of days, an episode of care lasted. The episode duration is a function of both the individual's care-seeking behavior and the physician's treatment plan for that individual. The mean, 25th percentile, and 75th percentile episode durations may be provided for each medical condition.

Episodes with MedMarker (percent): The percentage of all episodes attributed to a provider or provider group that had one or more MedMarker services present.

Severity of Illness: Conditions may be evaluated for Severity of Illness Level-1 (SOI-1) or S01-2, using these definitions:

SOU: routine, uncomplicated; represents the least physiologic progression (least severe).

S01-2: the disease may have local complications.

S01-3: the disease may involve multiple sites, or have systemic complications (most severe).

National MedMarker Comparative Database

To identify medical condition-specific MedMarkers and ensure accuracy and sufficient sample size, an exemplary National MedMarker Comparative Database may be applied to present the Percentage of Episodes with MedMarker service frequency to exemplary Specialist Panels' physicians.

The exemplary National MedMarker Comparative Database compiles claims data from a prespecified number (e.g. 25) of regions in the U.S. In this exemplary database:

The data represents two years of the most recent health insurance claims data.

Each region consists of at least a prespecified number (e.g. 200,000) members.

May tracks a prespecified (e.g. 64) MedMarkers spanning a prespecified number (e.g. 20) of specialty types.

Physicians preferably require a minimum number of episodes to be included in Percent of Episodes with MedMarker Service results (e.g. 10 episodes).

Some individual physicians included in the database may see large numbers of patients, and therefore represent practices similar to a physician group. For this reason one may see the term physician groups used in place of physicians.

Percentage of Episodes with MedMarker Service. This measure is:

One key to developing a protocol range is that this rate may help eliminate differences in billing patterns, thereby creating apples-to-apples comparison of frequency of MedMarkers.

Defined as the number of episodes with at least one MedMarker performed (i.e. percentage of episodes with services).

Example: A physician may perform arthroscopies on 35% of her episodes (or patients).

Another commonly calculated metric included in the exemplary National MedMarker Comparative Database is the Number of Services per prespecified (e.g. 1,000) Episodes. The Services per 1,000 Episodes metric can be important to understanding physician practice patterns, including billing patterns. However, this metric may not answer the question of how often a service should be performed, and therefore was not included in the exemplary National Specialist Panel Surveys.

The Role of the Exemplary National Specialist Panels

Exemplary nationwide panels of physicians may be organized by specialty type. Exemplary National Specialist Panels may consist of clinicians who:

Are board-certified in the specialty or sub-specialty of interest.

Have practiced 5-30 years after residency.

Spend at least 75% of their time in direct clinical practice and patient care.

Have a current academic affiliation with a U.S. medical school found in the top recipients of National Institutes of Health clinical research funding for that medical specialty. Panels of 30 to 40 clinicians may be selected in each of the specialties represented in exemplary Clinical MedMarker Protocol Ranges. In some specialties, a good number of sub-specialists who tend to perform or order the procedure of interest are also selected.

Each panel member may be asked to review the following information:

Definitions of the medical conditions and severity of illness level of each patient population studied.

A definition of the MedMarker service of interest, including CPT codes.

A frequency chart of Percentage of Episodes with MedMarker Service derived from the exemplary National MedMarker Comparative Database.

The survey instrument then may ask questions to obtain appropriate clinical feedback.

Clinical MedMarker Protocol Range Methodology

The exemplary National Specialist Panels' results may be used to develop an exemplary Clinical MedMarker Protocol Ranges, which are an achievable range for physician practice based on specialty-specific clinical input. The results from the members of a National Specialist Panel are input into a computer system and statistics are calculated utilizing a computer system based on those inputs. Two examples are shown for each of two specialties.

Cardiology

Overview. 40 cardiologists were identified to participate in the exemplary Clinical MedMarker Protocol Range survey. All were affiliated with U.S. medical schools that rank among the top 40 recipients of National Institutes of Health clinical research funding for that medical specialty:

Example #1.1: Irritable Colon (SOI-1)—Colonoscopy

Brief Description of Condition: Irritable Colon SOU includes irritable bowel syndrome and functional diarrhea. Irritable Colon SOI-1 does not include functional digestive diseases, diverticula of intestines, and noninfectious gastroenteritis or colitis.

Average Duration: 25 days.

MedMarker of Interest: Colonoscopy.

Associated CPT Codes: 45355-45392.

Specialist Panel: N=31 gastroenterologists surveyed

Percent of Episodes with MedMarker Service Statistics:

| Mean | Median | Mode | 25th | 50th | 75th |
|---|---|---|---|---|---|
| 11% | 15% | 0% | 0% | 15% | 20% |

Clinical MedMarker Protocol Range

| Clinical MedMarker Protocol Range | |
|---|---|
| Irritable Colon (SOI-1)<br>MedMarker: Colonoscopy | 0%-15% |

Question 1: Upper Bound

| | Standard Statistics | | | | | Percentile | | |
|---|---|---|---|---|---|---|---|---|
| | Mean | S.D. | Min | Max | Median | 25th | 50th | 75th |
| All Respondents (10% outliers removed) | 14% | 7% | 5% | 30% | 15% | 10% | 15% | 15% |
| West | 16% | 7% | 5% | 30% | 15% | N/A | N/A | N/A |
| Central | 15% | N/A | 15% | 15% | 15% | N/A | N/A | N/A |
| Midwest | 8% | 8% | 0% | 15% | 10% | N/A | N/A | N/A |
| East | 15% | 12% | 5% | 45% | 15% | N/A | N/A | N/A |
| South | 20% | 17% | 5% | 45% | 15% | N/A | N/A | N/A |

Question 2: Lower Bound

| | Standard Statistics | | | | | Percentile | | |
|---|---|---|---|---|---|---|---|---|
| | Mean | S.D. | Min | Max | Median | 25th | 50th | 75th |
| All Respondents (10% outliers removed) | 4% | 5% | 0% | 15% | 5% | 0% | 5% | 5% |
| West | 8% | 8% | 0% | 20% | 5% | N/A | N/A | N/A |
| Central | 10% | N/A | 10% | 10% | 10% | N/A | N/A | N/A |
| Midwest | 2% | 3% | 0% | 5% | 0% | N/A | N/A | N/A |
| East | 4% | 7% | 0% | 25% | 0% | N/A | N/A | N/A |
| South | 13% | 18% | 0% | 40% | 5% | N/A | N/A | N/A |

Example #1.2: Noninfectious Gastroenteritis (SOI-1)—CT Abdomen/Pelvis

Brief Description of Condition: Noninfectious Gastroenteritis SOI-1 includes non-infectious gastroenteritis, pseudopolyposis of the colon, and eosinophilic gastroenteritis. Noninfectious Gastroenteritis SOI-1 does not include eosinophilic or ulcerative colitis, peritonitis, regional enteritis, Crohn's disease, irritable bowel syndrome, or functional diarrhea.

Average Duration: 6 days
MedMarker of Interest: CT abdomen/pelvis
Associated CPT Codes: 72191-72194; 74150-74178
Specialist Panel: N=31 gastroenterologists surveyed Percent of Episodes with MedMarker Service Statistics:

| Mean | Median | Mode | 25th | 50th | 75th |
|---|---|---|---|---|---|
| 5% | 5% | 0% | 0% | 5% | 10% |

Clinical MedMarker Protocol Range

| Clinical MedMarker Protocol Range | |
|---|---|
| Noninfectious Gastroenteritis (SOI-1)<br>MedMarker: CT abdomen/pelvis | 0%-10% |

Question 1: Upper Bound

| | Standard Statistics | | | | | Percentile | | |
|---|---|---|---|---|---|---|---|---|
| | Mean | S.D. | Min | Max | Median | 25th | 50th | 75th |
| All Respondents (10% outliers removed) | 9% | 3% | 5% | 15% | 10% | 5% | 10% | 10% |
| West | 9% | 6% | 0% | 20% | 10% | N/A | N/A | N/A |
| Central | 15% | N/A | 15% | 15% | 15% | N/A | N/A | N/A |
| Midwest | 7% | 6% | 0% | 10% | 10% | N/A | N/A | N/A |
| East | 11% | 9% | 3% | 40% | 10% | N/A | N/A | N/A |
| South | 11% | 3% | 10% | 15% | 10% | N/A | N/A | N/A |

Question 2: Lower Bound

| | Standard Statistics | | | | | Percentile | | |
|---|---|---|---|---|---|---|---|---|
| | Mean | S.D. | Min | Max | Median | 25th | 50th | 75th |
| All Respondents (10% outliers removed) | 2% | 3% | 0% | 10% | 0% | 0% | 0% | 2% |
| West | 6% | 7% | 0% | 20% | 5% | N/A | N/A | N/A |
| Central | 10% | N/A | 10% | 10% | 10% | N/A | N/A | N/A |
| Midwest | 0% | 0% | 0% | 0% | 0% | N/A | N/A | N/A |
| East | 1% | 3% | 0% | 10% | 0% | N/A | N/A | N/A |
| South | 3% | 2% | 0% | 5% | 4% | N/A | N/A | N/A |

Orthopedics

Overview 40 orthopedists were identified to participate in the Clinical MedMarker Protocol Range survey. All were affiliated with U.S. medical schools that rank among the top 40 recipients of National Institutes of Health clinical research funding for that medical specialty:

Example #2.1: Bursitis of Upper Limb (SOI-1)—MRI Joint Extremities

Brief Description of Condition: Bursitis of Upper Limb SOI-1 includes bursitis of the olecranon, epicondylitis, ganglion, and tenosynovitis of the hand. Bursitis of Upper Limb SOH does not include enthesopathies, rotator cuff syndrome, or rupture of tendon or synovium.

Average Duration: 38 days
MedMarker of Interest: MRI Joint Extremities
Associated CPT Codes: 73221-73223, 73721-73723
Specialists Panel: =40 orthopedists surveyed Percent of Episodes with MedMarker Service Statistics:

| Mean | Median | Mode | 25th | 50th | 75th |
|---|---|---|---|---|---|
| 18% | 15% | 15% | 10% | 15% | 25% |

Clinical MedMarker Protocol Range

| Clinical MedMarker Protocol Range | |
|---|---|
| Bursitis of Upper Limb (SOI-1) | 0%-20% |
| MedMarker: MRI joint extremities | |

Question 1: Upper Bound

| | Standard Statistics | | | | | Percentile | | |
|---|---|---|---|---|---|---|---|---|
| | Mean | S.D. | Min | Max | Median | 25th | 50th | 75th |
| All Respondents (10% outliers removed) | 22% | 9% | 10% | 40% | 20% | 15% | 20% | 30% |
| West | 24% | 18% | 0% | 55% | 25% | N/A | N/A | N/A |
| Central | 27% | 23% | 5% | 70% | 25% | N/A | N/A | N/A |
| Midwest | 27% | 6% | 20% | 30% | 30% | N/A | N/A | N/A |
| East | 26% | 14% | 0% | 50% | 30% | N/A | N/A | N/A |
| South | 18% | 10% | 5% | 40% | 15% | N/A | N/A | N/A |

Question 2: Lower Bound

| | Standard Statistics | | | | | Percentile | | |
|---|---|---|---|---|---|---|---|---|
| | Mean | S.D. | Min | Max | Median | 25th | 50th | 75th |
| All Respondents (10% outliers removed) | 7% | 5% | 0% | 20% | 5% | 5% | 5% | 10% |
| West | 15% | 17% | 0% | 45% | 5% | N/A | N/A | N/A |
| Central | 4% | 4% | 0% | 10% | 5% | N/A | N/A | N/A |
| Midwest | 10% | 0% | 10% | 10% | 10% | N/A | N/A | N/A |
| East | 12% | 9% | 0% | 30% | 10% | N/A | N/A | N/A |
| South | 4% | 2% | 0% | 5% | 5% | N/A | N/A | N/A |

Example #2.2: Low Back Pain (SOI-1)—MRI Spine

Brief Description of Condition: Low Back Pain 50I-1 includes ankylosing spondylitis, spondylopathy, and sprain/strain along the thoracic to coccyx. Low Back Pain 50I-1 does not include schmorl's nodes, spondylosis, postlaminectomy syndrome, disc displacement, or malignancies. There may be minor physiological progression of spinal stenosis or disc degeneration, but these diagnoses have not been documented.

Average Duration: 21 days

MedMarker of Interest: MRI spine

Associated CPT Codes: 72141, 72142, 72146-72149, 72156-72158

Specialists Panel: N=40 orthopedists surveyed

Percent of Episodes with MedMarker Service Statistics:

| Mean | Median | Mode | 25th | 50th | 75th |
|---|---|---|---|---|---|
| 25% | 20% | 0% | 10% | 20% | 40% |

Clinical MedMarker Protocol Range

| Clinical MedMarker Protocol Range | |
|---|---|
| Low Back Pain (SOI-1) | 0%-20% |
| MedMarker: MRI spine | |

Question 1: Upper Bound

| | Standard Statistics | | | | | Percentile | | |
|---|---|---|---|---|---|---|---|---|
| | Mean | S.D. | Min | Max | Median | 25th | 50th | 75th |
| All Respondents (10% outliers removed) | 19% | 6% | 10% | 35% | 20% | 15% | 20% | 20% |
| West | 16% | 10% | 0% | 35% | 15% | N/A | N/A | N/A |
| Central | 23% | 10% | 10% | 40% | 20% | N/A | N/A | N/A |
| Midwest | 20% | 0% | 20% | 20% | 20% | N/A | N/A | N/A |
| East | 26% | 18% | 5% | 75% | 20% | N/A | N/A | N/A |
| South | 19% | 12% | 5% | 50% | 20% | N/A | N/A | N/A |

Question 2: Lower Bound

| | Standard Statistics | | | | | Percentile | | |
|---|---|---|---|---|---|---|---|---|
| | Mean | S.D. | Min | Max | Median | 25th | 50th | 75th |
| All Respondents (10% outliers removed) | 7% | 5% | 0% | 20% | 5% | 5% | 5% | 10% |
| West | 8% | 10% | 0% | 30% | 5% | N/A | N/A | N/A |
| Central | 7% | 6% | 0% | 15% | 10% | N/A | N/A | N/A |
| Midwest | 7% | 6% | 0% | 10% | 10% | N/A | N/A | N/A |
| East | 14% | 15% | 0% | 55% | 10% | N/A | N/A | N/A |
| South | 7% | 8% | 0% | 25% | 5% | N/A | N/A | N/A |

Figure 11:
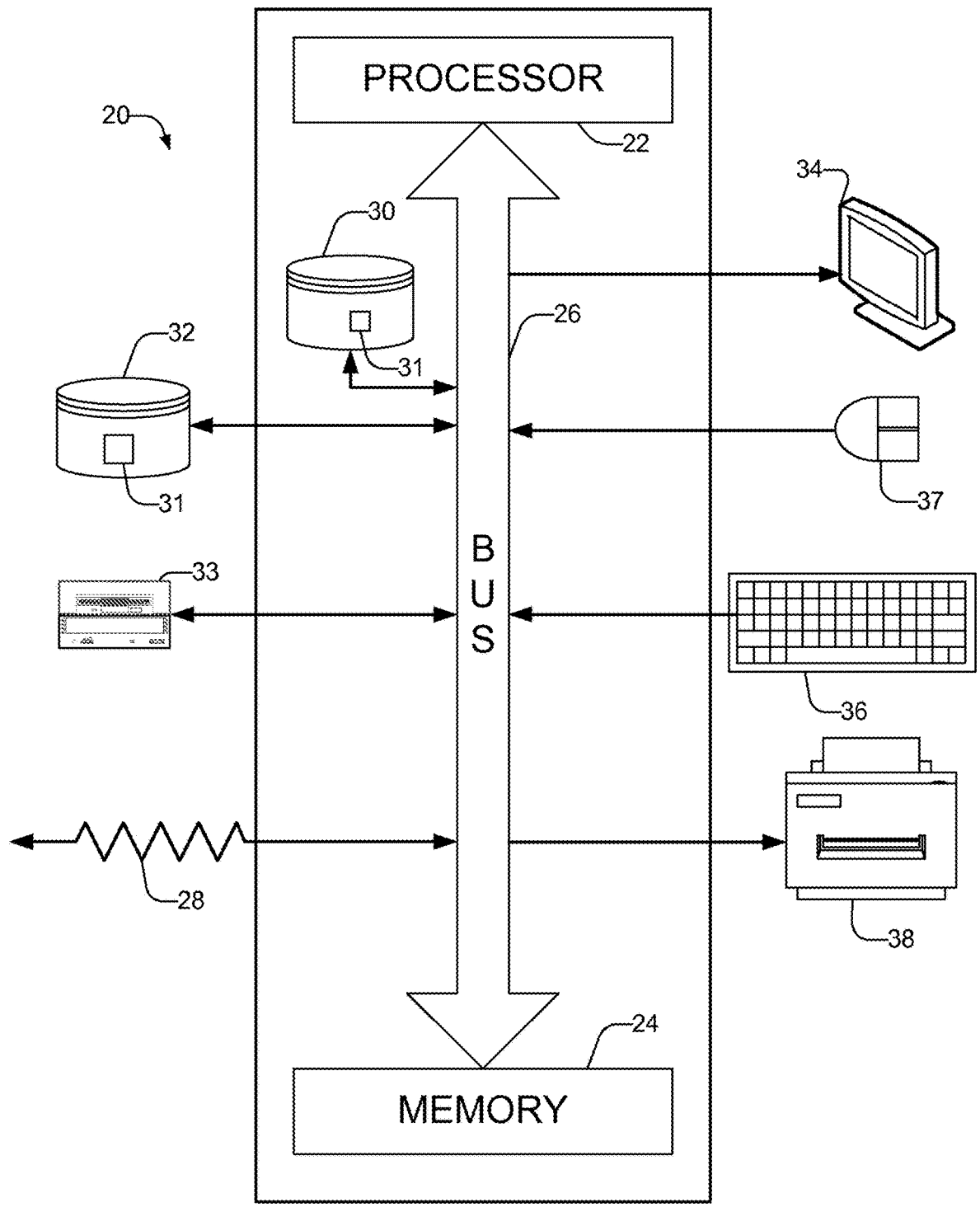
FIG. 11 is a block diagram illustrating a computer system that may be utilized to implement the present disclosure, as shown in FIGS. 9 and 10.

FIG. 11 is a block diagram illustrating a General Purpose Computer, such as utilized to implement the present invention, as shown in FIGS. 9 and 10. The General Purpose Computer 20 has a Computer Processor 22 (CPU), and Memory 24, connected by a Bus 26. Memory 24 is a relatively high speed machine readable medium and includes Volatile Memories such as DRAM, and SRAM, and Non-Volatile Memories such as, ROM, FLASH, EPROM, EEPROM, and bubble memory. Also connected to the Bus are Secondary Storage 30, External Storage 32, output devices such as a monitor 34, input devices such as a keyboard 36 with a mouse 37, and printers 38. Secondary Storage 30 includes machine-readable media such as hard disk drives, magnetic drum, and bubble memory. External Storage 32 includes machine-readable media such as floppy disks, removable hard drives, magnetic tape, CD-ROM, and even other computers, possibly connected via a communications line 28. The distinction drawn here between Secondary Storage 30 and External Storage 32 is primarily for convenience in describing the invention. As such, it should be appreciated that there is substantial functional overlap between these elements. In addition, one or more client computing devices 29 may be connected to computer system 20 via communications line 28, which may be, for example, an Internet connection. Computer software such operating systems, utilities, user programs, and software to implement the present invention and data files can be stored in a Computer Software Storage Medium, such as memory 24, Secondary Storage 30, and External Storage 32. Executable versions of computer software 33, such as software utilized to implement the present invention can be read from a Non-Volatile Storage Medium such as External Storage 32, Secondary Storage 30, and Non-Volatile Memory and loaded for execution directly into Volatile Memory, executed directly out of Non-Volatile Memory, or stored on the Secondary Storage 30 prior to loading into Volatile Memory for execution.

Computer-Implemented Methods and Graphical User Interface (GUI) to Support Decision-Makers in Complex Evaluations Computer system 20 may also be used to implement methods and a graphical user interface that guide decision-makers for health plans and/or medical care providers through a tiered analysis and distillation of the claim line item information in a CLI file. The disclosed methods and graphical user interface are tailored to guide the decision-maker to objective indications of the patterns of practice most suitably targeted for process-of-care improvement, both in general (e.g., across all medical care providers in a plan) and specifically (for particular medical care providers), as well as in the selection and understanding of meaningful thresholds for more complex evaluations of medical care providers. The methods and graphical user interface achieve this through a series of steps that distills the many thousands or millions of claim line item records in the CLI file into an objective, repeatable, clinically supported evaluation of medical care providers within a selected medical specialty, and generates one or more structured outputs, in a concise, easily comprehended format, that not only provide the decision-maker with an outcome, but guide the decision-maker to a detailed understanding of the precise impact of underlying patterns of practice on the outcome. In some examples, the disclosed methods and graphical user interface are further tailored to guide the decision-maker in the selection, understanding, and/or application of meaningful thresholds for more complex evaluations for medical care providers, such as a determination of whether to relax prior authorization rules for a particular medical care provider and/or an identification of precise areas for improvement that would make the medical care provider eligible for relaxation of prior authorization rules.

Figure 12:
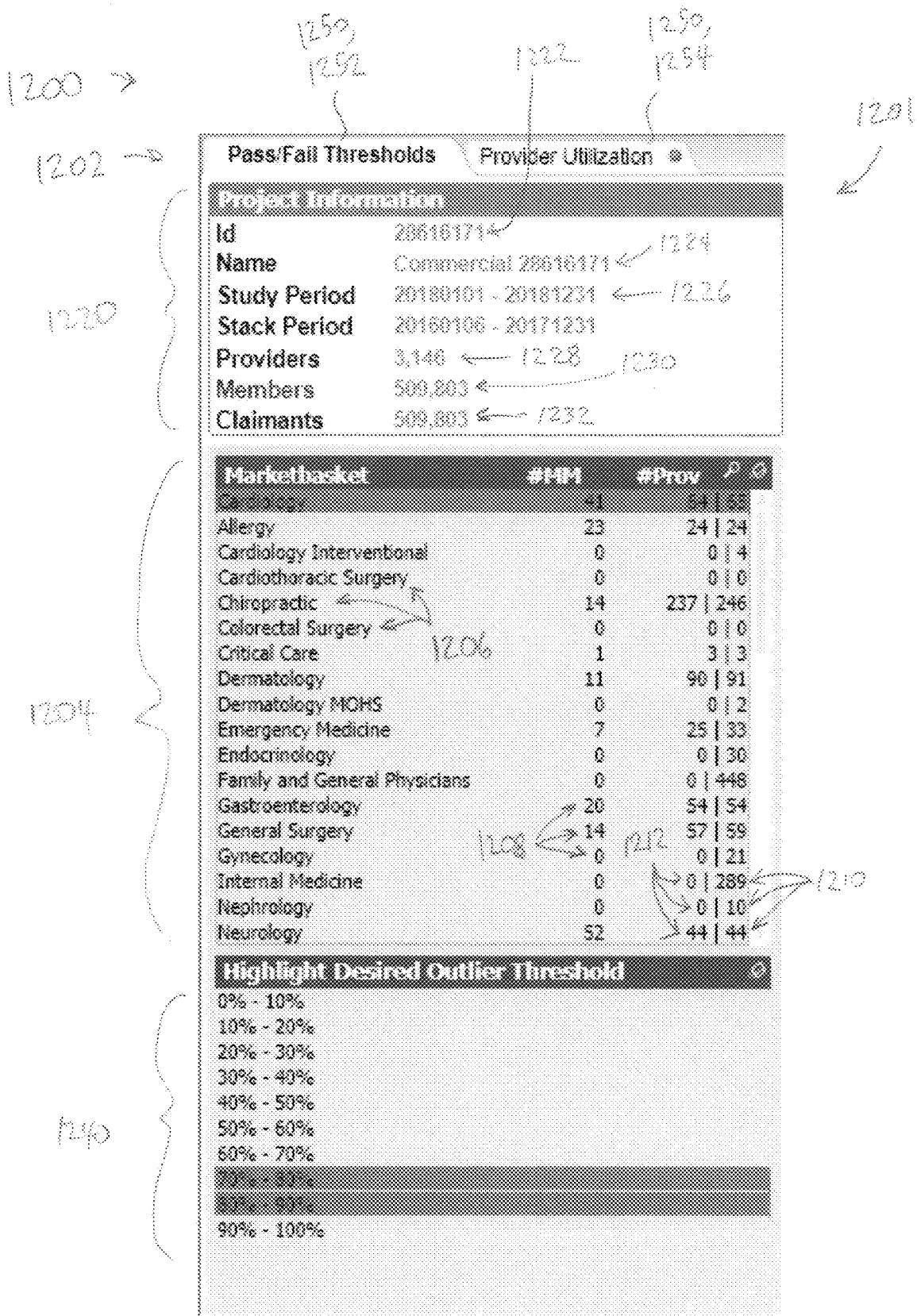
FIG. 12 is an example first pane of a graphical user interface (GUI) that may be caused to be displayed by the computer system shown in FIG. 11.

FIG. 12 is an example first pane 1202 of a graphical user interface (GUI) 1200 that may be caused to be displayed by processor 22. GUI 1200 is a tool for use by decision-makers of a health plan or healthcare provider organization in evaluating a plurality of healthcare providers against process-of-care standards For example, processor 22 may cause GUI 1200 to display on monitor 34. For another example, processor 22 may cause GUI 1200 to display on a display screen of client computing device 29 via Internet communication with client computing device 29, such as when computer system 20 functions as an application server.

In some examples, first pane 1202 displays a configuration display tier 1201. In the illustrated example, configuration display tier 1201 includes a specialty control 1204 that enables a selection, via a user input device, such as keyboard 36, mouse 37, or a touchscreen (not shown) of computer system 20 or equivalent input devices of client computing device 29, of a medical specialty 1206 from among a plurality of medical specialties 1206. GUI 1200 is programmed to guide the user through the evaluation against process-of-care standards for medical care providers in the selected medical specialty 1206. In the example, specialty control 1204 is a list box with a scroll bar that enables the user to view a list of available medical specialties 1206, and select one by clicking the mouse, tapping on the touch screen, or using tab and arrow keys. Alternatively, specialty control 1204 is implemented in any suitable fashion that enables GUI 1200 to function as described herein.

Each of the medical specialties associated with specialty control 1204 is associated in a memory device, such as memory 24, secondary storage 30, or external storage 32, with one or more pairs of medical conditions and marker code groups. In the example, each of the marker code groups includes one or more related codes from among a set of standard codes each used to report a corresponding one of a medical, surgical, or diagnostic procedure or service in the claim line item CLI records, as discussed above. In other words, each marker code group is either a single procedure or service code, or two or more codes comprising variations of a same procedure or service. In some examples, at least 40 such codes are present in the claim line item (CLI) information used in the evaluation presented by GUI 1200. Moreover, as noted above, there are typically hundreds or thousands of codes (e.g., CPT-4 codes) used to cover a wide variety of services across various medical specialties, and in some examples a significant proportion (or nearly all) of these codes may be present in the CLI information. Each of the one or more marker code groups associated with each medical condition may be referred to in combination as a "marker-condition pair."

In the example, the set of medical conditions evaluated for each medical specialty matches the medical conditions in the marketbasket for the respective medical specialty 1206, as described above, and the marker code groups are similar to the MedMarkers as described above. However, the marker code groups are not derived as the few services most relevant to the efficiency of each particular medical provider, but are predefined (i.e., stored in the memory device) as a more expansive set of services that together encompass the most relevant medical conditions and associated services for all (or almost all) of the medical providers in the respective medical specialty. Alternatively, the set of medical conditions and the associated one or more marker code groups are selected in any suitable fashion that enables GUI 1200 to function as described herein. It should be understood that the set of medical conditions may include two or more medical conditions having the same "name" but a different severity of illness (SOI), as discussed above (e.g., the set of medical conditions for cardiology may include two separate medical conditions "Congestive heart failure—SOI 1" and "Congestive heart failure—SOI 2" each having an independent set of marker-condition pairs).

In the example, specialty control 1204 further displays additional information including a number 1208 of marker-condition pairs associated with each medical specialty 1206, as well as a total number 1210 of medical care providers for which episodes of care corresponding to the medical specialty are present in the CLI information under analysis, and a qualifying number 1212 of medical care providers that meet a qualifying standard, as discussed in more detail below, for a meaningful evaluation with respect to the medical specialty 1206. Alternatively, specialty control 1204 further displays any suitable additional information, or no additional information.

In some examples, configuration display tier 1201 also includes a project information header 1220. Project information header 1220 displays summary information about the evaluation derived from the CLI file. For example, project information header 1220 includes a numeric identifier 1222 and name 1224 assigned to the CLI file and/or the current evaluation of the CLI file. In some such examples, the CLI file is specific to claims filed with a given health plan by a variety of medical care providers, with each medical care provider corresponding to a healthcare provider organization (e.g., hospital system or medical office). Accordingly, numeric identifier 1222 and name 1224 may correspond to an identifier and name of the health plan. In other such examples, the CLI file is specific to claims filed by a variety of medical care providers in a given geographic region (e.g., the northeast United States). Accordingly, numeric identifier 1222 and name 1224 may correspond to an identifier and name of the geographic region. Alternatively, numeric identifier 1222 and name 1224 are any suitable values that enable GUI 1200 to function as described herein.

In the illustrated example, project information header 1220 also includes a study period 1226 covered by the claim line items in the CLI file, a number 1228 of providers associated with the services provided in the CLI file, a number 1230 of members covered by the health plan corresponding to the CLI file during the study period, and a number of claimants 1232 represented in the CLI file. Alternatively, project information header 1220 includes any suitable summary information about the evaluation derived from the CLI file. In other examples, project information header 1220 is included within configuration display tier 1201 at a location separate from first pane 1202, or configuration display tier 1201 does not include project information header 1220.

In some examples, configuration display tier 1201 also includes a pass/fail highlight control 1240 that controls highlighting of certain pass/fail summary indicators in pass/fail threshold tier 1302 of GUI 1200, as will be described in more detail below with respect to protocol-range outlier table 1304 (shown in FIG. 13). In the illustrated example, pass/fail highlight control 1240 is a list box control that displays ranges 1242 of percentages, and enables one or more of the displayed ranges 1242 to be selected. Alternatively, pass/fail highlight control 1240 is implemented in any suitable fashion that enables GUI 1200 to function as described herein. In other examples, pass/fail highlight control 1240 is included within configuration display tier 1201 at a location separate from first pane 1202, or configuration display tier 1201 does not include pass/fail highlight control 1240.

In some examples, first pane 1202 also includes a second-pane control 1250 operable to select content to be displayed in a second pane 1300 of GUI 1200. In the illustrated example, second-pane control 1250 includes a pass/fail threshold control 1252 and a utilization summary control 1254. More specifically, GUI 1200 is programmed to display pass/fail threshold tier 1302 (shown in FIG. 13) and some additional aspects of configuration display tier 1201 in second pane 1300 in response to a selection, via the user input device, of pass/fail threshold control 1252, and to display both a providers summary display tier 1402 and a services summary display tier 1452 (shown in FIG. 14) in second pane 1300 in response to a selection, via the user input device, of utilization summary control 1254. In other examples, second-pane control 1250 is operable to select any suitable content to be displayed in second pane 1300 that enables GUI 1200 to function as described herein.

In the illustrated example, second-pane control 1250 is implemented as a tab-selection control, i.e., pass/fail threshold control 1252 and utilization summary control 1254 are implemented as tab controls along a top edge of first pane 1202. Alternatively, second-pane control 1250 is implemented in any suitable fashion that enables GUI 1200 to function as described herein.

Figure 13:
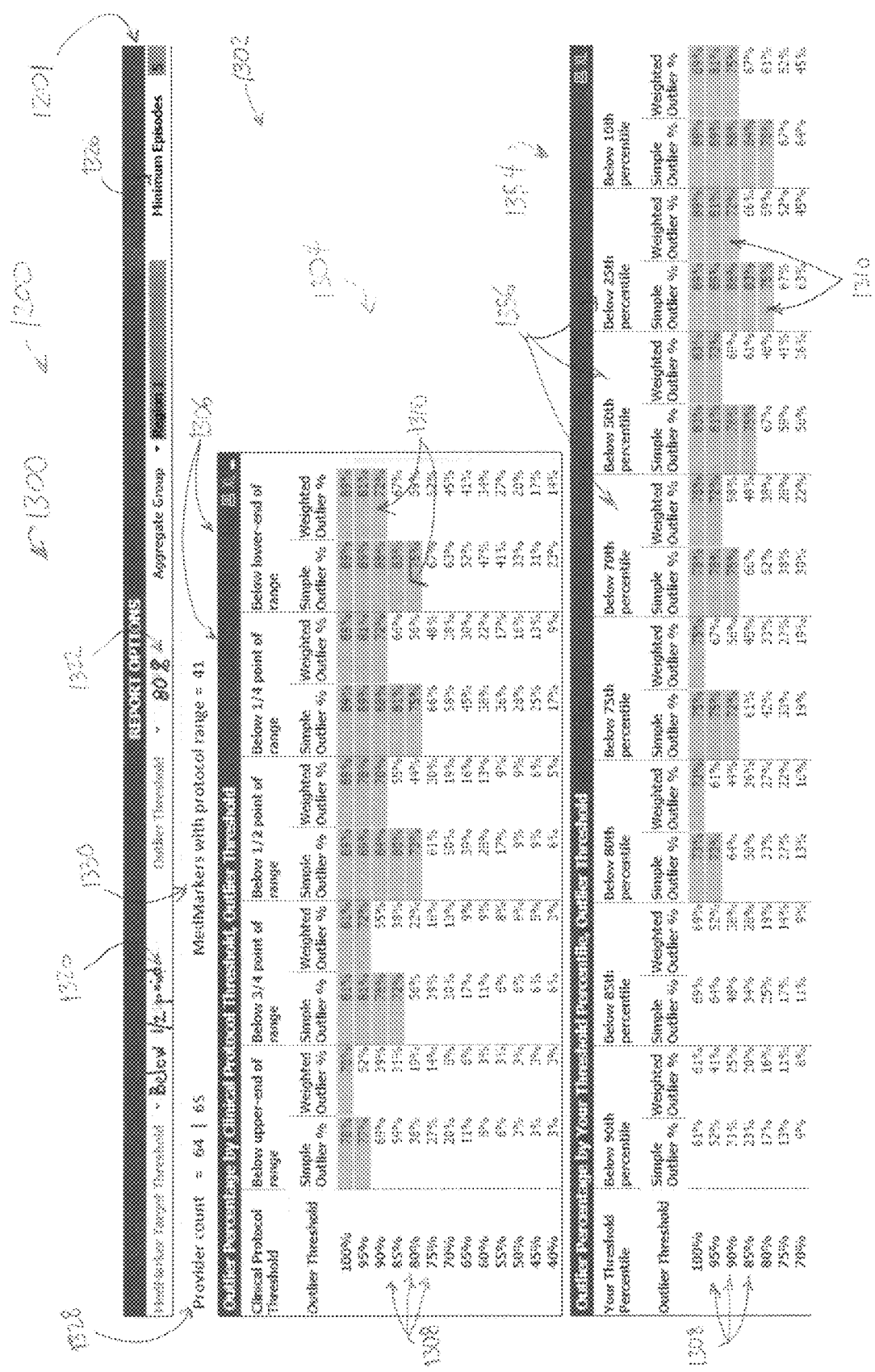
FIG. 13 is an example second pane of the GUI of FIG. 12 that may be caused to be displayed by the computer system shown in FIG. 11.

FIG. 13 is an example second pane 1300 of GUI 1200 that may be caused to be displayed by processor 22. In some examples, GUI 1200 is programmed to present first pane 1202 and second pane 1300 of the configuration display tier simultaneously on the display device (e.g., monitor 34 or a display screen of client computing device 29). For example, first pane 1202 is displayed on a left-hand side of the display device, and second pane 1300 is displayed on a right-hand side. Alternatively, first pane 1202 and second pane 1300 are displayed other than simultaneously.

In the illustrated example, second pane 1300 is displaying pass/fail threshold tier 1302 and certain additional aspects of configuration display tier 1201 in response to the selection, via the user input device, of pass/fail threshold control 1252 (shown in FIG. 12). Pass/fail threshold tier 1302 includes a protocol-range outlier table 1304 that summarizes performance across medical providers represented in the CLI file for the medical specialty 1206 that was selected using specialty control 1204 (shown in FIG. 12). Performance is evaluated by processor 22 based on a predefined set of protocol ranges associated, in the memory device, with each marker-condition pair in the selected medical specialty. The protocol range for each marker-condition pair includes a clinically supported lower bound and upper bound of a process-of-care standard for the rate of utilization of the associated marker code group for episodes of the associated medical condition.

In some examples, the protocol ranges are determined with reference to the national database and/or panels of experts in the medical specialty, as described above. Alternatively, the protocol ranges are determined in any suitable fashion that enables GUI 1200 to function as described herein.

Protocol-range outlier table 1304 includes columns 1306 corresponding to potential target points for comparison to the rate of utilization of the associated marker code group for episodes of the associated medical condition. The potential target points may include points both within and outside the protocol range. For example, columns 1306 include "Below upper end of range" (i.e., all rates of utilization that do not exceed the upper bound of the protocol range are deemed to "satisfy" or "pass" the target point for the marker-condition pair), "Below ¾ point of range," (i.e., all rates of utilization that do not exceed a rate that is ¾ of the way from the lower bound to the upper bound are deemed to "satisfy" or "pass" the target point for the marker-condition pair), "Below ½ point of range," "Below ¼ point of range," and "Below lower end of range." Alternatively, columns 1306 include any suitable set of potential target points that enable GUI 1200 to function as described herein.

Protocol-range outlier table 1304 also includes rows 1308 corresponding to potential outlier thresholds. The outlier thresholds are a compliance point for the performance of each medical care provider across marker-condition pairs. More specifically, for each provider, processor 22 is programmed to compare the provider's actual rate of utilization to the target point defined by column 1306, and aggregate the comparisons across marker-condition pairs to determine an overall score for the respective medical care provider. The value in each row 1308 is the percentage of medical care providers (that qualify for evaluation under the selected medical specialty) having an overall score, based on the potential target point in column 1306, that fails to meet the outlier threshold for the row. For example, rows 1308 include outlier thresholds of 100% (i.e., any provider that fails to achieve an overall score of 100% across marker-condition pairs is an "outlier"), 90% (i.e., any provider that fails to achieve an overall score of 90% across marker-condition pairs is an "outlier"), etc. Alternatively, rows 1308 include any suitable set of outlier thresholds that enable GUI 1200 to function as described herein.

In the example, each column 1306 is subdivided into a simple outlier percentage, based on a simple overall score for each provider, and a weighted outlier percentage, based on a weighted overall score for each provider. In general, within the step of aggregating the comparisons across marker-condition pairs to determine an overall score, the simple overall score weights the comparison of the provider's actual rate of utilization against the target point equally for each marker-condition pair, while the weighted overall score weights the comparison of the provider's actual rate of utilization against the target point more heavily for marker-condition pairs for which the provider has more episodes of the associated medical condition and/or for which the associated service(s) in the marker code group has a higher bundle cost. Alternatively, columns 1306 are not subdivided into simple and weighted outlier percentages. For example, GUI 1200 is programmed to provide only one type of overall score.

In some examples, processor 22 calculates the simple overall score by calculating a ratio of a number of the marker-condition pairs having the "pass" status with respect to the target point in column 1306 to a sum of the number of the marker-condition pairs having the pass status and a number of the marker-condition pairs having the fail status. Moreover, in some examples, processor 22 calculates the weighted overall score by weighting the status of each marker-condition pair proportionately to the bundle cost of the associated marker code group as applied to a number of episodes of the associated medical condition attributable to the medical care provider. For example, the overall weighted score is calculated by summing, for each marker-condition pair that passes the target point comparison in column 1306, the product of the number of episodes of the medical condition and the bundle cost of the service to obtain a numerator; summing, for all marker-condition pairs regardless of pass or fail, the product of the number of episodes of the medical condition and the bundle cost of the service to obtain a denominator; and obtaining the weighted overall score in percentage form from the numerator and the denominator. Alternatively, the simple overall score and the weighted overall score are calculated in any suitable fashion that enables GUI 1200 to function as described herein.

In some examples, certain cells 1310 of protocol-range outlier table 1304 are highlighted based on a comparison of the cell values to the selected ranges 1242 in pass/fail highlight control 1240 (shown in FIG. 12). More specifically, if the value in cell 1310 lies within the one or more selected ranges 1242, the cell 1310 is highlighted. The term "highlighting" includes any visual emphasis applied to the cell 1310 relative to other, non-highlighted cells, such as a difference in fill color or font color. Alternatively, cells 1310 are not highlighted.

As noted above, in some examples, second pane 1300 may also include certain aspects of configuration display tier 1201. In particular, in the illustrated example, configuration display tier 1201 also includes a target control 1320 that enables a selection, via the user input device, of a target point definition to be used for more detailed analysis within GUI 1200. In other words, while protocol-range outlier table 1304 displays summary results across multiple potential target points in columns 1306, the single target point selected in target control 1320 is applied by processor 22 to produce more detailed analyses of performance with respect to a particular medical care provider and/or a particular medical specialty, as will be described in more detail below.

In the example, target control 1320 is implemented as a drop-down control that includes a list of each potential target point included in columns 1306. Additionally or alternatively, a selection in target control 1320 may be set by clicking the mouse on, tapping on the touch screen on, or using tab and arrow keys to arrive at the heading of the corresponding column 1306. In other examples, target control 1320 is implemented in any suitable fashion that enables GUI 1200 to function as described herein. Moreover, in certain other examples, target control 1320 is provided within configuration display tier 1201 at a location other than second pane 1300.

Configuration display tier 1201 further includes an outlier threshold control 1322 that enables a selection, via the user input device, of an outlier threshold associated with a first level of performance, also to be used for more detailed analysis within GUI 1200. In other words, while protocol-range outlier table 1304 displays summary results with respect to multiple potential outlier thresholds in rows 1308, the single outlier threshold selected in outlier threshold control 1322 is applied by processor 22 to produce more detailed analyses of performance with respect to a particular medical care provider and/or a particular medical specialty, as will be described in more detail below.

In the example, outlier threshold control 1322 is implemented as a drop-down control that includes a list of each potential outlier threshold included in rows 1308. Additionally or alternatively, a selection in outlier threshold control 1322 may be set by clicking on, tapping the touchscreen on, or using the tab and arrow keys to arrive at the heading of the corresponding row 1308. In other examples, outlier threshold control 1322 is implemented in any suitable fashion that enables GUI 1200 to function as described herein. Moreover, in certain other examples, outlier threshold control 1322 is provided within configuration display tier 1201 at a location other than second pane 1300.

In some examples, configuration display tier 1201 also includes a qualifying-standard control 1326 that enables a selection, by the user input device, of a qualifying standard that must be met by each medical care provider, with respect to each selected marker-condition pair, in order for the marker-condition pair to be included in the evaluation of the overall score. Alternatively, qualifying-standard control 1326 is located within configuration display tier 1201 at a location other than on second pane 1300, or configuration display tier 1201 does not include qualifying-standard control 1326.

In some examples, the qualifying standard corresponds to a minimum number of episodes of the medical condition associated with a marker-condition pair that must be attributable to the medical care provider in order for the overall score for the medical care provider to include the provider's performance for that marker-condition pair. In other words, qualifying-standard control 1326 enables the user to input a numeric value for the minimum number of episodes, and processor 22 is programmed to compare, for each medical condition of the set of medical conditions associated with the selected medical specialty, the minimum number of episodes to an actual number of the episodes of the medical condition in the CLI file attributable to the medical care provider. Alternatively, the qualifying standard corresponds to any suitable criterion that enables GUI 1200 to function as described herein.

In certain examples, in response to the minimum number of episodes exceeding the actual number of episodes, processor 22 is programmed to assign a "non-qualifying" status (e.g., rather than a "pass" or "fail" status) to each marker-condition pair for the corresponding medical condition, and each marker-condition pair having the non-qualifying status is subsequently given zero weight during the step of aggregating the statuses across the marker-condition pairs to obtain an overall score. In certain other examples, in response to the minimum number of episodes exceeding the actual number of episodes, processor 22 is programmed to insert substitute placeholder values for the marker-condition pair in lieu of the medical care provider's own performance for that marker-condition pair, and include those substitute values in the aggregation across marker-condition pairs. For example, the substitute value may be the peer group average value for that marker-condition pair (i.e., if the medical care provider has not treated sufficient episodes of a medical condition during the study period, the evaluation substitutes the peer group average performance for the one or more marker-condition pairs associated with that medical condition). Alternatively, processor 22 is programmed to take any suitable action in response to the minimum number of episodes exceeding the actual number of the episodes that enables GUI 1200 to function as described herein In the illustrated example, qualifying-standard control 1326 is implemented as a numeric-entry field. Alternatively, qualifying-standard control 1326 is implemented in any suitable fashion that enables GUI 1200 to function as described herein.

In the example, configuration display tier 1201 additionally includes a provider-count display field 1328 that reproduces the qualifying number 1212 and total number 1210 (shown in FIG. 12) of medical care providers for the medical specialty selected in specialty control 1204 (shown in FIG. 12), as well as a pair-count display field 1330 that reproduces the number 1208 of marker-condition pairs associated with the selected medical specialty. Alternatively, configuration display tier 1201 does not include provider-count display field 1328 and/or pair-count display field 1330.

It should be appreciated that the specific structure of protocol-range outlier table 1304 visually and procedurally aids the decision-maker in selecting a relevant target point via target point control 1320, and a relevant outlier threshold via outlier threshold control 1322. In order for decision-makers to arrive at, and convincingly support, a meaningful evaluation of medical care providers against a process-of-care standard, it is exceedingly important to select thresholds and standards that uncover meaningful differentiators within the overwhelming mass of data in a typical CLI file, which may contain many thousands or millions of records each arising from a single procedure or service. In other words, a seemingly common-sense outlier threshold and/or target point for a level of performance may prove insupportable if it results in a too-high proportion of the medical care providers being classified as "outliers." Protocol-range outlier table 1304 enables decision-makers to view a distribution of the percentage of medical care providers that become "outliers" across the range of potential target points in columns 1306 and the range of potential outlier thresholds across rows 1308, which provides a compact and intuitive tool for selecting a relevant target point via target point control 1320, and a relevant outlier threshold via outlier threshold control 1322. In some examples, the highlighting of cells 1310 based on the selected ranges 1242 in pass/fail highlight control 1240 provides further visual guidance, as cells along the border between highlighted and non-highlighted cells may indicate locations where the potential target points and outlier thresholds produce meaningful results.

Although protocol-range outlier table 1304 provides advantages in some examples as described above, it should also be understood that additional advantages provided by GUI 1200 inhere even in examples in which GUI 1200 does not include protocol-range outlier table 1304.

In some examples, pass/fail threshold tier 1302 includes a plan-percentile outlier table 1354 in addition to, or as an alternative to, protocol-range outlier table 1304. Similar to protocol-range outlier table 1304, plan-percentile outlier table 1354 summarizes performance across medical providers represented in the CLI file for the medical specialty 1206 that was selected using specialty control 1204 (shown in FIG. 12). However, rather than columns 1306 representing potential target points defined with reference to the predefined set of protocol ranges for each marker-condition pair, plan-percentile outlier table 1354 includes columns 1356 representing the potential target points defined with reference to percentile ranking within a range of actual rates of utilization of the marker-condition pair by medical care providers in the health plan. In other words, rather than a predefined, clinically supported lower bound and upper bound of a process-of-care standard for the rate of utilization of the associated marker code group for episodes of the associated medical condition, plan-percentile outlier table 1354 relies upon the distribution of actual utilization rates by medical care providers in the health plan's own data. In the example, plan-percentile outlier table 1354 includes rows 1308 for potential outlier thresholds and highlighted cells 1310 implemented in like fashion as described above for protocol-range outlier table 1304. Accordingly, in some examples plan-percentile outlier table 1354 provides similar advantages to those described above with respect to protocol-range outlier table 1304.

Figure 14:
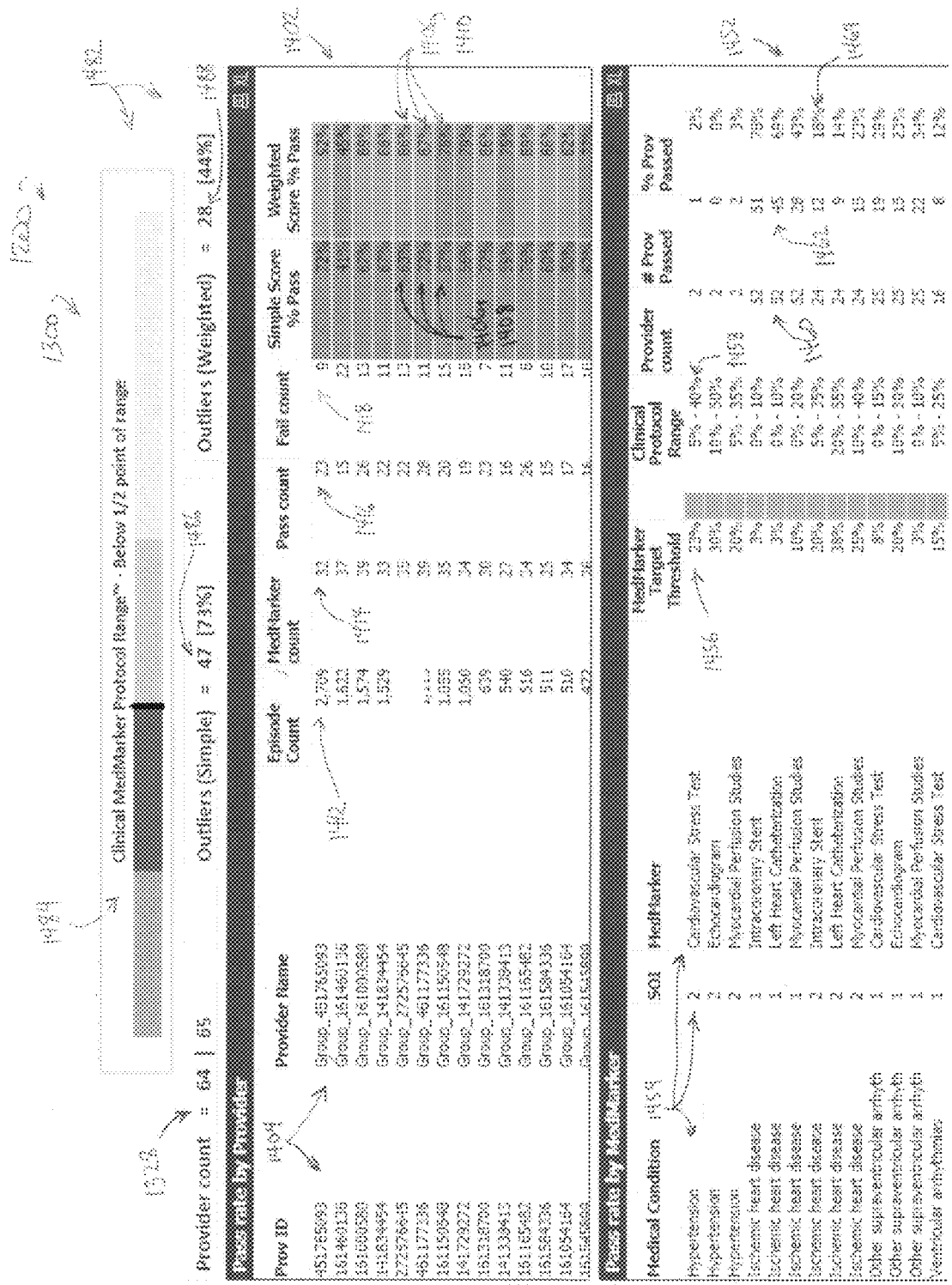
FIG. 14 is another example second pane of the GUI of FIG. 12 that may be caused to be displayed by the computer system shown in FIG. 11.

FIG. 14 is another example second pane 1300 of GUI 1200 that may be caused to be displayed by processor 22. In the illustrated example, second pane 1300 is displaying both providers summary display tier 1402 and services summary display tier 1452 in response to a selection, via the user input device, of utilization summary control 1254 on configuration display tier 1201. Alternatively, GUI 1200 is programmed to present providers summary display tier 1402 and services summary display tier 1452 separately in second pane 1300, for example in response to additional options included in second pane control 1250, or in any suitable location. In the example, GUI 1200 displays a summary area 1482 along with providers summary display tier 1402 and services summary display tier 1452. Alternatively, summary area 1482 is not included with providers summary display tier 1402 and/or services summary display tier 1452.

Providers summary display tier 1402 includes a listing 1404 of medical care providers in the selected medical specialty 1206 that meet a qualifying standard for at least one pair of the one or more marker-condition pairs associated with the medical specialty. In the example, listing 1404 includes both a unique numeric provider ID and a provider name for each of the medical care providers. Alternatively, listing 1404 includes any suitable information regarding each medical care provider that enables GUI 1200 to function as described herein. In some examples, each listed medical care provider is an aggregation of individual practitioners, e.g., affiliated with the same hospital system or healthcare office. In some such examples, the aggregation includes individual practitioners affiliated with multiple healthcare provider entities, but all associated with (e.g., submitting claims to) a single health plan. Additionally or alternatively, the aggregation of individual practitioners is associated with a geographic region. In other examples, each listed medical care provider is an individual practitioner.

In the example, the qualifying standard applied is the one selected using qualifying-standard control 1326 on configuration display tier 1201, such as a minimum number of episodes of the associated medical condition for at least one marker-condition pair. Alternatively, the qualifying standard is selected in any suitable fashion that enables GUI 1200 to function as described herein. In certain examples, the qualifying standard may be selected to cause all medical care providers represented in the CLI file to be evaluated.

Providers summary display tier 1402 also includes an identification of an overall score 1406 for each of the listed medical care providers. As discussed above with respect to pass/fail threshold tier 1302, processor 22 determines the overall score 1406 for each listed medical care provider 1404 by determining, for each qualifying marker-condition pair, an actual utilization rate of the marker code group in episodes of care for the corresponding medical condition of the pair. A specific marker-condition pair "qualifies" if the associated medical condition meets the qualifying standard (e.g., if the respective medical care provider has handled at least the minimum number of episodes of the associated medical condition).

For example, processor 22 parses the CLI file to find episodes of the medical condition attributable to each medical care provider, and to find instances of utilization of the corresponding marker code group within each episode. It should be understood that a single episode of care for a medical condition may encompass any number of individual claim line items, as each claim line item refers to a single procedure or service arising during the course of care for the medical condition. In some examples, the CLI file stored in the memory device already includes supplemental indexing fields assigning each claim line item to an episode, as discussed above. In other examples, processor 22 applies a suitable grouping algorithm to assign each claim line item in the CLI file to an episode of care. Alternatively, processor 22 derives the actual utilization rate from the claim line item information in any suitable fashion that enables GUI 1200 to function as described herein. In some examples, configuration display tier 1201 includes a control (not shown) that enables a selection, via the user input device, from among a plurality of measurement options for the actual rate of utilization.

The actual rate of utilization of a procedure or service is measurable in a number of ways. In some examples, the actual rate of utilization is based on a percentage of the episodes of care for the medical condition attributable to the medical care provider in which any of the one or more related codes of the associated marker code group was utilized. In other examples, the actual rate of utilization is based on a total number of instances of utilization of any of the one or more related codes of the associated marker code group per a specified number of episodes of care of the associated medical condition (e.g., instances per 1,000 episodes). In other examples, the actual rate of utilization is based on a total cost of utilization of any of the one or more related codes of the associated marker code group per a specified number of the episodes of care of the associated medical condition (e.g., cost per 1,000 episodes). In other examples, the actual rate of utilization is based on a total number of instances of utilization of any of the one or more related codes of the associated marker code group per number of patients treated by the medical care provider. In other examples, the actual rate of utilization is based on a total cost of utilization of any of the one or more related codes of the associated marker code group per number of patients treated by the medical care provider. In other examples, the actual rate of utilization by the medical care provider is based on a total number of instances of utilization of any of the one or more related codes of the associated marker code group per number of members treated by the medical care provider. More specifically, a member is an individual to whom health care coverage has been extended under a health plan, and treatment of a "member" includes treatment of any of one or more individuals included in the member's health care coverage under the health plan. In other examples, the actual rate of utilization is based on a total cost of utilization of any of the one or more related codes of the associated marker code group per number of members treated by the medical care provider. Alternatively, the actual rate of utilization is measured in any suitable fashion that enables GUI 1200 to function as described herein.

As discussed above with respect to pass/fail threshold tier 1302, processor 22 further determines the overall score 1406 for each listed medical care provider 1404 by comparing, for each at least one qualifying marker-condition pair, the actual utilization rate to the target point for the pair. In the example, processor 22 calculates the target point by applying the target point definition, selected in target control 1320 in configuration display tier 1201, to the predefined protocol range associated with the respective marker-condition pair in the memory device, as discussed above. Alternatively, processor 22 determines the target point for each marker-condition pair in any suitable fashion that enables GUI 1200 to function as described herein.

In some examples, the comparison for each marker-condition pair is a simple pass/fail-type comparison. More specifically, processor 22 is programmed to assign a status to each marker-condition pair from among a group of status options including (i) a "fail" status, assigned in response to the actual rate of utilization exceeding the target point for episodes of the associated medical condition, and (ii) a "pass" status, assigned in response to the actual rate of utilization not exceeding the target point. It should be understood that the "pass" and "fail" labels are for illustration only, and are not limiting. In the example, to enable the comparison of the target point to the actual utilization rate, the protocol ranges are stored in the memory device in the same unit of measurement (or if stored in different units, then converted by processor 22 to the same unit of measurement) that is programmed or selected to be used for the actual utilization rate. Accordingly, applying the target point definition to the protocol ranges provides the target point in the same units of measurement as the actual utilization rate, as discussed above.

In some examples, processor 22 is further programmed to assign a "non-qualifying" status to each marker-condition pair associated with any medical condition for which the medical care provider does not meet the qualifying standard, as discussed above. Again, the "non-qualifying" label is for illustration only, and is not limiting. In other examples, processor 22 is further programmed to assign a substitute "pass" or "fail" status (e.g., based on a peer group average for the marker-condition pair) to each marker-condition pair associated with any medical condition for which the medical care provider does not meet the qualifying standard, also as discussed above.

In some examples, the target point definition being applied is displayed to the user in a target definition display 1484 in summary area 1482 of second pane 1300. In the illustrated example, target definition display 1484 is indicated both textually (i.e., "Below ½ point of range") and graphically in a bar chart, in which the target point definition is illustrated as a vertical line within a shaded range between the lower and upper bounds of the protocol range. For example, the protocol range is shaded light green above the target point and dark green below the target point, regions above the upper bound are shaded light blue, and regions below the lower bound are shaded dark blue. In other examples, target definition display 1484 illustrates the target point definition being applied in any suitable fashion that enables GUI 1200 to function as described herein. Target definition display 1484 thus advantageously provides an easily comprehended reminder to the user of the criteria being used for the current evaluation of outliers. Alternatively, summary area 1482 does not include target definition display 1484.

As discussed above with respect to pass/fail threshold tier 1302, processor 22 additionally aggregates the comparisons for each marker-condition pair to determine the overall score 1406 for each listed medical care provider 1404. For example, processor 22 aggregates across marker-condition pairs to determine at least one of a simple overall score 1408 and a weighted overall score 1410, the calculations for which are described above with respect to protocol-range outlier table 1304 (shown in FIG. 13).

In the illustrated example, providers summary display tier 1402 displays both the simple overall score 1408 and the weighted overall score 1410 as the overall score 1406 for each listed medical care provider 1404. Alternatively, providers summary display tier 1402 displays only one of the simple overall score 1408 and the weighted overall score 1410 as the overall score 1406.

In some examples, processor 22 assigns an overall status to each listed medical care provider 1404. For example, the overall status is one of "outlier," in response to the overall score 1406 for the medical provider exceeding the outlier threshold, and "non-outlier," in response to the overall score 1406 for the medical provider not exceeding the outlier threshold. In the illustrated example, providers summary display tier 1402 reports the overall status for each listed medical care provider 1404 by selectively highlighting the overall score 1406. More specifically, the outlier status is illustrated by red highlighting of the overall score 1406, and the non-outlier status is illustrated by green highlighting of the overall score 1406. Alternatively, providers summary display tier 1402 reports the overall status for each listed medical care provider 1404 in any suitable fashion that enables GUI 1200 to function as described herein. Notably, the overall status for each listed medical care provider 1404 may differ based on whether the simple overall score 1408 or the weighted overall score 1410 is considered as the overall score 1406.

In some examples, processor 22 is programmed to apply the value of the outlier threshold selected in outlier threshold control 1322 of configuration display tier 1201. Alternatively, the outlier threshold applied by processor 22 is selected in any suitable fashion that enables GUI 1200 to function as described herein.

In some examples, providers summary display tier 1402 includes additional information that may be useful to a decision-maker in understanding and interpreting the evaluation produced by GUI 1200. In the illustrated example, providers summary display tier 1402 includes an episode count 1412 for each listed medical care provider 1404, representing a total number of episodes of care (for any medical condition in the set of medical conditions associated with the medical specialty 1206 selected using specialty control 1204) associated with the medical care provider in the CLI file. Also in the illustrated example, providers summary display tier 1402 includes a marker-condition pair count 1414, representing a number of marker-condition pairs associated with the medical specialty for which the listed medical care provider 1404 meets the qualifying standard for evaluation. Further in the illustrated example, providers summary display tier 1402 includes a pass count 1416 representing a number of marker-condition pairs associated with the medical specialty for which the listed medical care provider 1404 was assigned a "pass" status, and a fail count 1418 representing a number of marker-condition pairs associated with the medical specialty for which the listed medical care provider 1404 was assigned a "fail" status. Alternatively, providers summary display tier 1402 may include any suitable additional information that enables GUI 1200 to function as described herein.

In some examples, summary area 1482 also includes additional information that may be useful to a decision-maker in understanding and interpreting the evaluation produced by GUI 1200. In the illustrated example, summary area 1482 includes provider-count display field 1328 (also shown in FIG. 13), a count/percentage 1486 of medical care providers in the selected medical specialty that are outliers based on the simple overall score 1408, and a count/percentage 1488 of medical care providers in the selected medical specialty that are outliers based on the weighted overall score 1410. Alternatively, summary area 1482 may include any suitable additional information that enables GUI 1200 to function as described herein.

Figure 15:
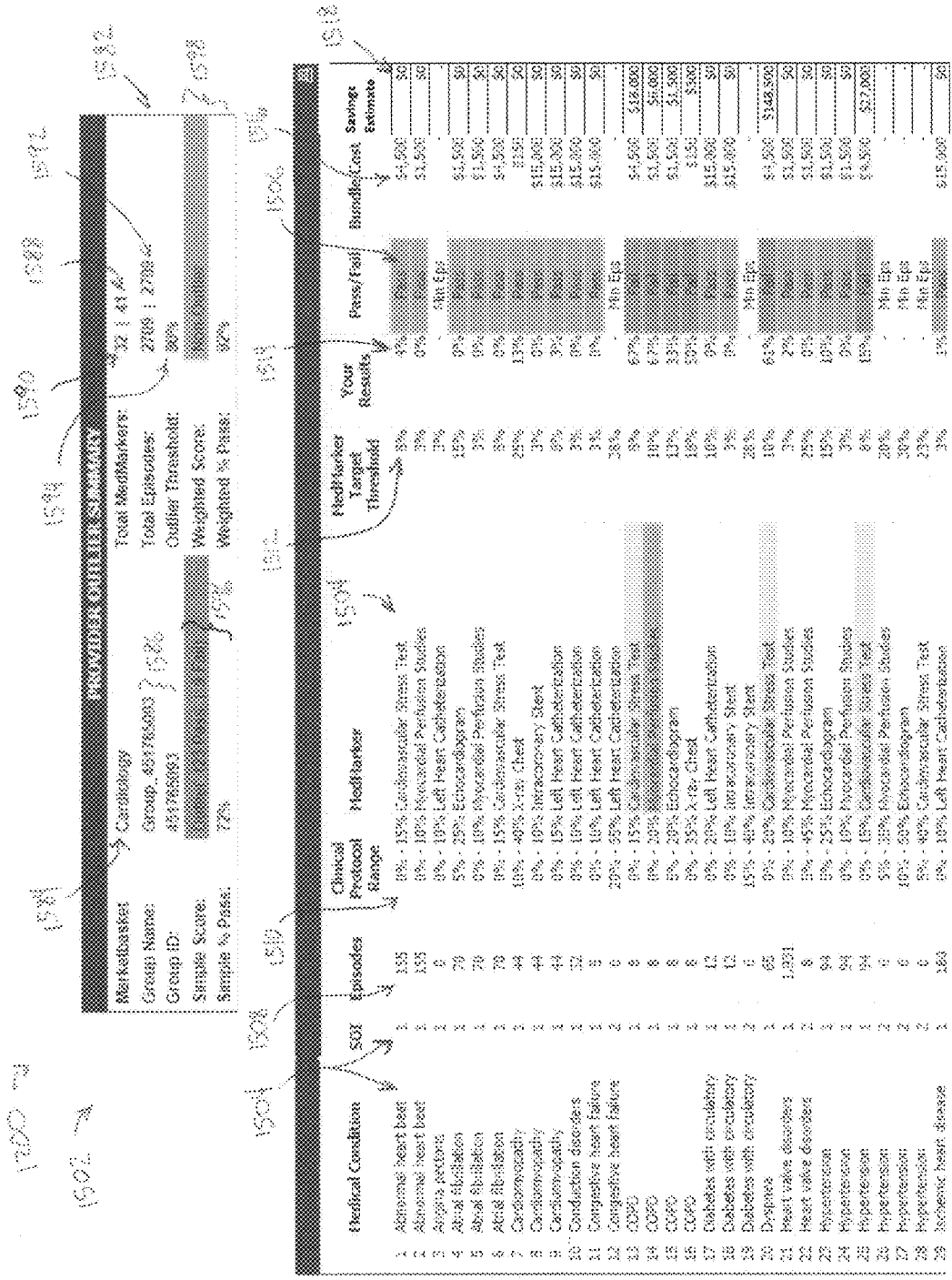
FIG. 15 is an example display screen of the GUI of FIG. 12 that may be caused to be displayed by the computer system shown in FIG. 11.

FIG. 15 is an example display screen including a provider detail display tier 1502 of GUI 1200. In some examples, provider detail display tier 1502 is displayable in response to a selection, via the user input device, of one of the listed medical care providers 1404 on providers summary display tier 1402 (shown in FIG. 14). For example, a listed medical care provider 1404 may be selected by clicking the mouse on, tapping on the touch screen on, or using tab and arrow keys to select a row of provider detail display tier 1502 corresponding to the listed medical care provider 1404. Additionally or alternatively, provider detail display tier 1502 is displayable in any suitable fashion that enables GUI 1200 to function as described herein. In certain examples, provider detail display tier 1502 is a separate screen of GUI 1200 that overlays, replaces, or is adjacent to first pane 1100 and second pane 1200. Alternatively, provider detail display tier 1502 is displayed in second pane 1200, for example simultaneously with first pane 1100.

Provider detail display tier 1502 includes a listing 1504 of each marker-condition pair for the selected medical care provider. In the example, listing 1504 includes a name (e.g., "Congestive heart failure") and an indicator of the severity of illness (SOI) (e.g., "1" or "2") of the associated medical condition, and a name of the associated marker code group (e.g., "Left heart Catheterization"), for each of the qualifying marker-condition pairs. Alternatively, listing 1504 includes any suitable information regarding each marker-condition pair that enables GUI 1200 to function as described herein.

Provider detail display tier 1502 also includes, for each listed marker-condition pair, an indication 1506 of the comparison of the actual rate of utilization to the target point for the marker-condition pair. In the illustrated example, indication 1506 includes the "pass," "fail," or "non-qualifying" (illustrated as "Min Eps," i.e., below the minimum episode threshold) status for the marker-condition pair, as well as the associated selective green and red highlighting, as discussed above. Alternatively, provider detail display tier 1502 includes any suitable indication 1506 of the comparison of the actual rate of utilization to the target point that enables GUI 1200 to function as described herein.

In some examples, provider detail display tier 1502 includes additional information that may be useful to a decision-maker in understanding and interpreting the evaluation produced by GUI 1200 for the selected medical care provider. In the illustrated example, provider detail display tier 1502 includes an episode count 1508 for each listed marker-condition pair 1504, representing a number of episodes of care for the associated medical condition that are attributable to the medical care provider in the CLI file. Also in the illustrated example, provider detail display tier 1502 includes the lower and upper bounds of the protocol range 1510 associated with the listed marker-condition pair 1504. Further in the illustrated example, provider detail display tier 1502 includes the target point 1512 for each listed marker-condition pair 1504, obtained by applying the target point definition (discussed above) to the protocol range 1510 as discussed above. Additionally in the illustrated example, provider detail display tier 1502 includes the actual rate of utilization 1514 of the selected medical care provider for each listed marker-condition pair 1504. Also in the illustrated example, provider detail display tier 1502 includes the bundle cost 1516 associated with a single utilization of the listed marker code group 1504, which may be associated with the marker code group in the memory device and retrieved by processor 22. Further in the illustrated example, provider detail display tier 1502 includes, for each marker-condition pair having the failed status, a cost of overuse 1518 of the associated marker code group. For example, processor 22 calculates the cost of overuse 1518 for each marker-condition pair 1504 having the failed status by applying (e.g., multiplying) the bundle cost 1516 to a product of the number of episodes 1508 of the associated medical condition and a difference between the actual rate of utilization 1514 and the target rate of utilization 1516 for the marker-condition pair. In other words, cost of overuse 1518 represents a cost savings available if the selected provider were to reduce its usage rate of the marker code group for episodes of the associated medical condition to the target point. Alternatively, provider detail display tier 1502 may include any suitable additional information that enables GUI 1200 to function as described herein.

In some examples, provider detail display tier 1502 includes automatic highlighting, within the listed marker-condition pairs 1504, of marker code groups associated with the largest value or values of cost of overuse 1518. In the illustrated example, the marker code group "Cardiovascular Stress Test" is associated with three listed marker-condition pairs 1504 having the failed status, which collectively have a cost of overuse of almost $200,000. In response, GUI 1200 automatically highlights each instance of the marker code group "Cardiovascular Stress Test" using a first color in listed marker-condition pairs 1504 having the failed status, and the first color is selected to draw the user's attention to this important driver of cost. Similarly, the marker code group "Myocardial Perfusion Studies" is associated with only one listed marker-condition pair 1504 having the failed status, which has a cost of overuse 1518 of $6,000. In response, GUI 1200 automatically highlights each (in this case, a single) instance of the marker code group "Myocardial Perfusion Studies" using a second color in listed marker-condition pairs 1504 having the failed status, and the second color is selected to draw the user's attention to this secondary driver of cost. In the illustrated example, other marker code groups associated with listed marker-condition pairs 1504 having the failed status each have a cost of overuse 1518 of less than $2,000, and are not highlighted due to the relatively low impact on cost. In other examples, GUI 1200 implements selection and prioritizing of marker code groups to highlight in listed marker-condition pairs 1504 in response to cost of overuse 1518 in any suitable fashion that enables GUI 1200 to function as described herein. Alternatively, GUI 1200 does not implement automatic highlighting of marker code groups in listed marker-condition pairs 1504 in response to cost of overuse 1518.

In some examples, GUI 1200 further displays a summary area 1582 along with provider detail display tier 1502. Alternatively, summary area 1582 is not included with provider detail display tier 1502. In the illustrated example, summary area 1582 includes an indicator 1584 of the selected medical specialty (e.g., selected using specialty control 1204 in configuration display tier 1202), an indicator 1586 of the selected medical care provider (e.g., selected from the list of medical care providers 1404 in providers summary display tier 1402), a total number 1588 of marker-condition pairs corresponding to the indicated medical specialty, a number 1590 of marker-condition pairs for which the selected medical care provider meets the qualifying standard for evaluation, a total number 1592 of episodes (for medical conditions associated with the selected medical specialty) attributable to the selected medical care provider in the CLI file, the selected outlier threshold 1594, the simple overall score and/or simple overall status 1596 for the selected medical care provider, and the weighted overall score and/or weighted overall status 1598 for the selected medical care provider. Alternatively, summary area 1582 may include any suitable additional information that enables GUI 1200 to function as described herein.

In some examples, a decision-maker may be guided by the overall status of a medical care provider, as developed and understood through the variety of tools to visualize and dynamically examine supporting information, provided by GUI 1200. As one non-limiting example, a decision-maker for a health plan may determine to relax prior authorization requirements for those medical care providers maintaining an overall status of "non-outlier," particularly when those providers have maintained the non-outlier status over a large number of total episodes. In other words, the non-outlier status indicates that the medical care provider has consistently operated within the clinically determined protocol ranges, or a desirable sub-range thereof, in utilizing the services and procedures most closely aligned with the associated medical specialty (as represented by the marker-condition pairs for the set of medical conditions associated in the memory device with the medical specialty). Because the evaluation and in-depth visualization tools provided by GUI 1200 are objective and consistent across all medical providers in the specialty and across time, the decision-maker may trust that the medical care providers maintaining the non-outlier status are not likely to over-utilize the most relevant services and procedures, rendering the administrative costs of prior authorization requirements unnecessary. Accordingly, GUI 1200 provides an improvement over conventional computer-implemented systems that parse claim line item information to evaluate a performance of medical care providers.

For illustrative purposes, some non-limiting examples of a decision-maker's use of the tools provided by GUI 1200 are as follows, with reference to FIGS. 12-15. In some examples, the decision-maker seeks to determine, on behalf of a health plan, which healthcare provider organizations in a region should qualify for a relaxation of prior authorization rules with respect to one or more medical specialties. The steps below could be performed in-house by the health plan, by a third-party consultant on behalf of the health plan, by any combination thereof, or by any suitable combination of users. In other examples, the decision-maker seeks to determine, on behalf of a healthcare provider organization, which areas of emphasis in bringing its practices within clinically supported process-of-care standards would better position the healthcare provider organization to request a relaxation of prior authorization rules with respect to one or more medical specialties. The steps below could be performed in-house by the healthcare provider organization, by a third-party consultant on behalf of the healthcare provider organization, by any combination thereof, or by any suitable combination of users. It should be understood that data regarding the performance of healthcare provider organizations is anonymized for purposes of the evaluations.

The user first accesses configuration display tier 1201 to set the parameters for an evaluation. The user reviews project information header 1220 for confirmation of the data source (e.g., CLI file) providing the basis of the evaluation. The user then selects a medical specialty 1206 for evaluation using specialty control 1204. In response to the selection, pass/fail threshold tier 1302, including protocol-range outlier table 1304 and/or plan-percentile outlier table 1354, is displayed. For example, specialty control 1204 is displayed in first pane 1202 and pass/fail threshold tier 1302 is displayed simultaneously in second pane 1302, and second pane 1302 updates to "fill in" cells of protocol-range outlier table 1304 and/or plan-percentile outlier table 1354 with corresponding values each time the user clicks on a different specialty in specialty control 1204.

Using pass/fail threshold tier 1302, the user reviews the cell values across rows 1308 of potential outlier thresholds and columns 1306 and/or 1356 of potential target points and selects a relevant target point via target point control 1320, and a relevant outlier threshold via outlier threshold control 1322, as discussed above. For example, the user may select ranges 1242 in pass/fail highlight control 1240 to obtain further visual guidance from the border between highlighted and non-highlighted cells as to where the potential target points and outlier thresholds produce meaningful results, also as discussed above. The user then selects utilization summary control 1254 to view providers summary display tier 1402, for example in second pane 1300.

Using providers summary display tier 1402, the user reviews the overall score 1406 (e.g., the simple overall score 1408 and/or the weighted overall score 1410) and the corresponding overall status (e.g., pass/fail) for each medical care provider, based on the criteria selected in configuration display tier 1201. To drill down into a particular medical care provider's evaluation, the user selects (e.g., clicks on) that medical care provider in list 1404 on providers summary display tier 1402 to view provider detail display tier 1502. The user reviews the listing 1504 of each marker-condition pair associated with the selected medical specialty to see the pass/fail indication 1506 for the selected medical care provider. The user may also review relevant background information, such as the episode count 1508 for each marker-condition pair 1504, the bundle cost 1516 for each marker-condition pair 1504, and in particular the estimated cost overrun for each "failed" marker-condition pair 1504. Based on this compact, concise, and easily managed summary and drill-down information provided by GUI 1200, the decision-maker may efficiently decide, on a per-specialty and per-provider basis, which healthcare provider organizations (i.e., medical care providers) merit relaxation of prior authorization rules in the specialty. Additionally or alternatively, the decision-maker may be able to present the medical care provider with an objective, concise, clinically supported set of objective goals (i.e., a set of marker-condition pairs and target points) that the medical care provider needs to meet or improve upon in order to qualify for relaxation of prior authorization. In other examples, the user may utilize additional, fewer, and/or different steps than those described above, and/or may use the tools provided by GUI 1200 for purposes other than relaxation of prior authorization rules.

Returning to FIG. 14, services summary display tier 1452 provides an alternative path, relative to providers summary display tier 1402, for a decision-maker to visualize and drill down into the evaluation. In particular, while providers summary display tier 1402 and provider detail display 1502 facilitate visualization and understanding of the evaluation on a per-provider basis, services summary display tier 1452 and service detail display tier 1602 (shown in FIG. 16) facilitate visualization and understanding of the evaluation on a per-marker-condition pair basis.

More specifically, services summary display tier 1452 includes a listing 1454 of marker-condition pairs associated with the selected medical specialty 1206. In the example, listing 1454 includes, for each listed marker-condition pair 1454, the name (e.g., "Hypertension") and an indicator of the severity of illness (SOI) (e.g., "1" or "2") of the associated medical condition, and a name of the associated marker code group (e.g., "Cardiovascular Stress Test"), similar to listing 1504 described above. Alternatively, listing 1454 includes any suitable information regarding each marker-condition pair that enables GUI 1200 to function as described herein.

Services summary display tier 1452 also includes the target point 1456 for each listed marker-condition pair 1454, obtained by applying the target point definition (discussed above) to the protocol range for the marker-condition pair, as discussed above. In some examples, services summary display tier 1452 also includes the lower and upper bounds of the protocol range 1458 associated with the listed marker-condition pair 1454, identical to protocol range 1510 in FIG. 15. Thus, target point 1456 is identical to target point 1512 in FIG. 15. As noted above, in certain examples, the target point definition being applied is displayed to the user in a target definition display 1484 in summary area 1482, e.g., also displayed in second pane 1300.

In some examples, services summary display tier 1452 further includes a count 1460 of medical care providers in the selected medical specialty 1206 that meet a qualifying standard for the listed marker-condition pair 1454. In the example, the qualifying standard applied is the one selected using qualifying-standard control 1326 on configuration display tier 1201, such as a minimum number of episodes of the associated medical condition for the listed marker-condition pair 1454. Alternatively, the qualifying standard is selected in any suitable fashion that enables GUI 1200 to function as described herein. In certain examples, the qualifying standard may be selected to cause all medical care providers represented in the CLI file to be evaluated for each listed marker-condition pair 1454. Moreover, services summary display tier 1452 includes a count 1462 of qualifying medical care providers that "pass" with respect to the listed marker-condition pair 1454, i.e., that have an actual rate of utilization for the listed marker-condition pair 1454 that does not exceed the target point 1456. The actual rate of utilization for each medical care provider may be determined by processor 22 parsing the CLI file, as described above. In some examples, services summary display tier 1452 further includes a pass rate 1464 determined by processor 22 by dividing the "pass" count 1462 by the total number of providers in the medical specialty, as shown for example in provider-count display field 1328 of summary area 1482. Alternatively, services summary display tier 1452 may include any suitable additional information that enables GUI 1200 to function as described herein.

Figure 16:
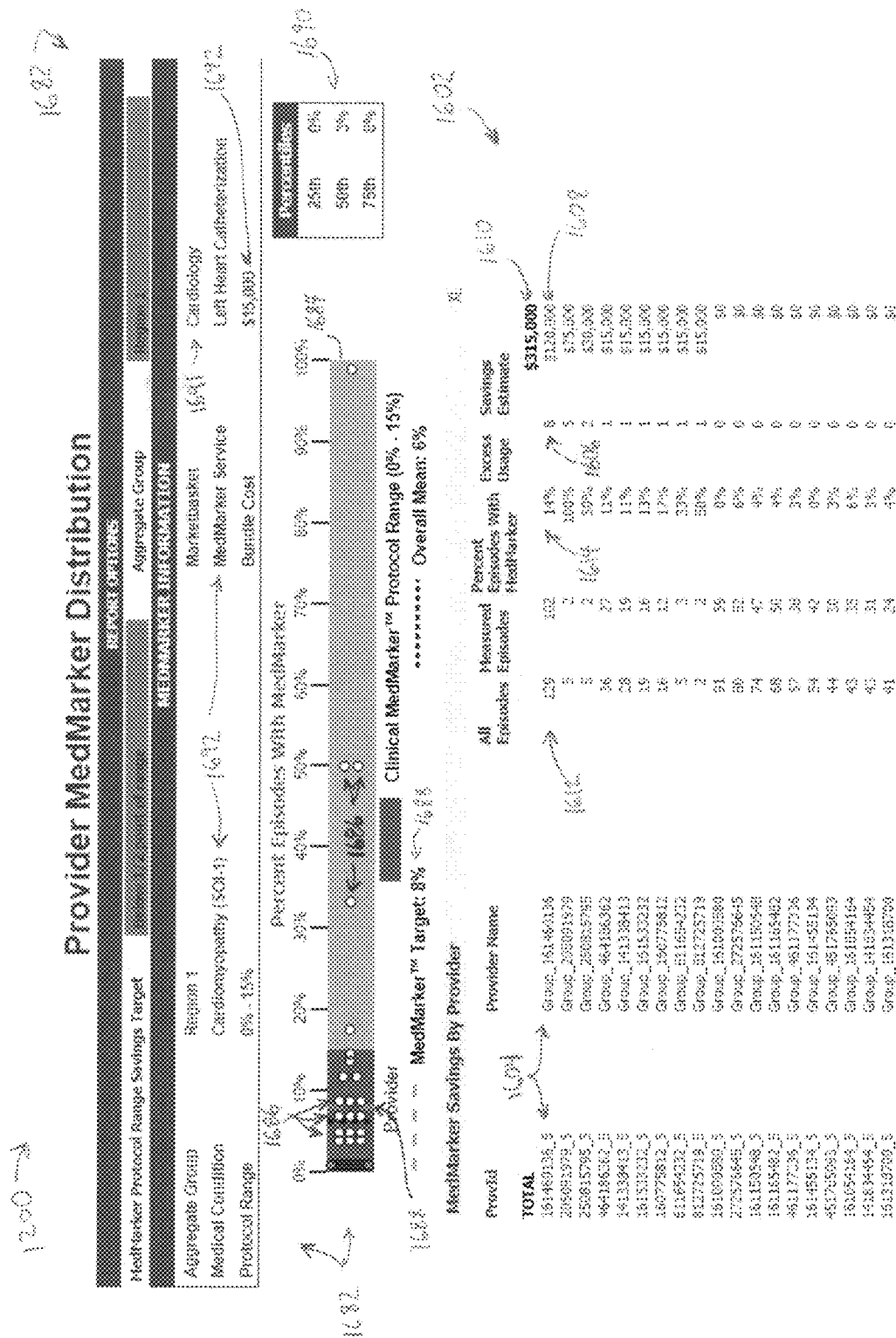
FIG. 16 is another example display screen of the GUI of FIG. 12 that may be caused to be displayed by the computer system shown in FIG. 11.

FIG. 16 is another example display screen including a service detail display tier 1602 of GUI 1200. In some examples, service detail display tier 1602 is displayable in response to a selection, via the user input device, of one of the listed marker-condition pairs 1454 on services summary display tier 1452 (shown in FIG. 14). For example, a listed marker-condition pair 1504 may be selected by clicking the mouse on, tapping on the touch screen on, or using tab and arrow keys to select a row of services summary display tier 1452 corresponding to the listed marker-condition pair 1504. Additionally or alternatively, service detail display tier 1602 is displayable in any suitable fashion that enables GUI 1200 to function as described herein. In certain examples, service detail display tier 1602 is a separate screen of GUI 1200 that overlays, replaces, or is adjacent to first pane 1100 and second pane 1200. Alternatively, service detail display tier 1602 is displayed in second pane 1200, for example simultaneously with first pane 1100.

Service detail display tier 1602 includes a listing 1604 of medical care providers in the selected medical specialty 1206 that meet a qualifying standard for the selected marker-condition pair 1454. In the example, listing 1604 includes both a unique numeric provider ID and a provider name for each of the medical care providers. Alternatively, listing 1604 includes any suitable information regarding each medical care provider that enables GUI 1200 to function as described herein. In some examples, as noted above, each listed medical care provider is an aggregation of individual practitioners, e.g., affiliated with the same hospital system or healthcare office. In some such examples, the aggregation includes individual practitioners affiliated with multiple healthcare provider entities, but all associated with (e.g., submitting claims to) a single health plan. In other examples, each listed medical care provider is an individual practitioner.

In the example, the qualifying standard applied is the one selected using qualifying-standard control 1326 on configuration display tier 1201, such as a minimum number of episodes of the associated medical condition for the selected marker-condition pair 1454. Alternatively, the qualifying standard is selected in any suitable fashion that enables GUI 1200 to function as described herein. In certain examples, the qualifying standard may be selected to cause all medical care providers represented in the CLI file to be evaluated for the selected marker-condition pair 1454.

Service detail display tier 1602 also includes, for each of the listed qualifying medical care providers 1604, an indication 1606 of an amount of excess usage of the marker code group of the selected marker-condition pair 1454 with respect to episodes of the medical condition of the selected pair 1454. In some examples, processor 22 determines the amount of the indicated excess usage 1606 by parsing the CLI file stored in memory device to determine the actual rate of utilization of the marker code group in episodes of the medical condition attributed to the respective listed qualifying medical care provider 1604, as discussed above, and comparing the target point 1456 (shown in FIG. 14) for the selected pair 1454 to the actual rate of utilization. For example, processor 22 is programmed to subtract the target point 1456 from the actual rate of utilization. In the case of a zero or negative result (i.e., the actual utilization does not exceed the target point), there is no overuse and processor 22 may set the indication 1606 to zero or some other null value. In the case of a positive result (i.e., the actual utilization exceeds the target point), processor 22 multiplies the result by the number of episodes of the associated medical condition attributed to the listed qualifying medical care provider 1604 to obtain a number of instances of overuse of the associated marker code group as the indication 1606. Alternatively, indication 1606 is a simple pass/fail indication, or is calculated by processor 22 in any suitable fashion that enables GUI 1200 to function as described herein.

In some examples, service detail display tier 1602 also includes, for each of the listed qualifying medical care providers 1604, an estimated monetary savings 1608 realizable in response to a reduction of the actual rate of utilization to match the target point 1456. For example, processor 22 is programmed to multiply the number of instances of overuse by the bundle cost associated with a single instance of utilization of the marker code group (discussed above with respect to FIG. 15) to determine estimated monetary savings 1608. Alternatively, processor 22 determines estimated monetary savings 1608 in any suitable fashion that enables GUI 1200 to function as described herein.

In some examples, GUI 1200 is programmed to sort listing of qualifying medical care providers 1604 by an amount of the estimated monetary savings 1608, enabling the decision-maker to more easily visualize and understand a distribution of an impact of the selected marker-condition pair 1454 on potential savings that could accrue across medical care providers 1604 from improved adherence to clinically supported process-of-care standards for the selected marker-condition pair 1454. Alternatively, GUI 1200 is programmed to sort listing of qualifying medical care providers 1604 in any suitable fashion that enables GUI 1200 to function as described herein.

In some examples, GUI 1200 is programmed to display a sum 1610 of the estimated monetary savings 1608 across the listing of qualifying medical care providers 1604, enabling the decision-maker to more easily visualize and understand an extent of the impact of the selected marker-condition pair 1454 on potential savings that could accrue across medical care providers 1604 from improved adherence to clinically supported process-of-care standards for the selected marker-condition pair 1454. For example, sum 1610 is included in a column heading associated with estimated monetary savings 1608. Alternatively, sum 1610 is displayed in any suitable location, or GUI 1200 does not include sum 1610.

In some examples, service detail display tier 1602 includes additional information that may be useful to a decision-maker in understanding and interpreting the evaluation produced by GUI 1200 for the selected marker-condition pair. In the illustrated example, service detail display tier 1602 includes an episode count 1612 for each listed qualifying medical care provider 1604, representing a number of episodes of care for the medical condition associated with the selected marker-condition pair 1454 that are attributable to the medical care provider in the CLI file. Also in the illustrated example, service detail display tier 1602 includes an indication 1614 of the actual rate of utilization, by the listed medical care provider 1604, of the marker code group associated with the selected marker-condition pair 1454. In the illustrated example, indication 1614 is expressed as a percentage of the episode count 1612 to facilitate a visual comparison with the target point. Alternatively, indication 1614 is expressed in any suitable fashion that enables GUI 1200 to function as described herein. In other examples, service detail display tier 1602 may include any suitable additional information that enables GUI 1200 to function as described herein.

In some examples, GUI 1200 further displays a summary area 1682 along with service detail display tier 1602. Alternatively, summary area 1682 is not included with service detail display tier 1602. In some examples, summary area 1682 includes an actual utilization distribution graphic 1684 that illustrates a distribution of the actual rate of utilization across the listed medical care providers 1604. In the illustrated embodiment, actual utilization distribution graphic 1684 is displayed as a bar chart, in which the target point 1688 is illustrated as a vertical line within a shaded range between the lower and upper bounds of the protocol range for the selected marker-condition pair 1454. For example, the protocol range is shaded dark green, regions outside the protocol range are shaded light blue, and the target point 1688 is a light green dashed line. In the illustrated embodiment, target point 1688 is also shown textually. Actual utilization distribution graphic 1684 further includes a graph point 1686 (e.g., a dot or circle) corresponding to indication 1614 of the actual rate of utilization for each listed medical care provider 1604. Selecting graph point 1686 automatically highlights the corresponding listed medical care provider 1604 in service detail display tier 1602, and vice versa. Alternatively, actual utilization distribution graphic 1684 is displayed in any suitable fashion that enables GUI 1200 to function as described herein.

Also in the illustrated example, summary area 1682 includes a percentile table 1690 indicating the actual rate of utilization at predefined percentiles (e.g., 25th, 50th, 75th) across the listed medical care providers 1604. Alternatively, summary area 1682 does not include percentile table 1690.

Further in the illustrated example, summary area 1682 includes an indicator 1691 of the selected medical specialty (e.g., selected using specialty control 1204 in configuration display tier 1202), an indicator 1692 of the selected marker-condition pair (e.g., selected from the list of marker-condition pairs 1454 in services summary display tier 1452), and the bundle cost 1693 for the marker code group associated with the selected marker-condition pair. Alternatively, summary area 1682 may include any suitable additional information that enables GUI 1200 to function as described herein.

For illustrative purposes, some additional non-limiting examples of a decision-maker's use of the tools provided by GUI 1200 are as follows, with reference to FIGS. 12-14 and 16. In some examples, the decision-maker seeks to determine, on behalf of a health plan, which strategies of emphasis in bringing practices within clinically supported process-of-care standards would most effectively improve outcomes against expenditures across healthcare provider organizations providing services covered under the health plan. For example, the health plan may have a limited amount of resources to devote to education and training in process-of-care standards, and may wish to focus those resources in a fashion that will provide the most benefit. The steps below could be performed in-house by the health plan, by a third-party consultant on behalf of the health plan, by any combination thereof, or by any suitable combination of users.

The user first accesses configuration display tier 1201 to set the parameters for an evaluation, such as by selecting a medical specialty 1206 for evaluation using specialty control 1204 and utilizing pass/fail threshold tier 1302, including protocol-range outlier table 1304 and/or plan-percentile outlier table 1354, to select a relevant target point via target point control 1320 and a relevant outlier threshold via outlier threshold control 1322, as discussed in more detail with respect to the examples described above. The user then selects utilization summary control 1254 to view services summary display tier 1452, for example in second pane 1300.

Using services summary display tier 1452, the user reviews the performance for each listed marker-condition pair 1454 across medical providers (e.g., pass rate 1464), as determined by comparison to the target point 1456 for each marker-condition pair 1454, based on the criteria selected in configuration display tier 1201. To drill down into performance by the medical care providers with respect to a particular marker-condition pair, the user selects (e.g., clicks on) that marker-condition pair in list 1454 on services summary display tier 1452 to view service detail display tier 1602. The user reviews the listing 1604 of each medical care provider associated with the selected medical specialty to see the estimated monetary savings 1608 associated with the medical care provider, and/or reviews the sum 1610 of the estimated monetary savings 1608 across the listing of qualifying medical care providers 1604. The user may also review relevant background information, such as the distribution of the actual rate of utilization across the listed medical care providers 1604 via actual utilization distribution graphic 1684, and the bundle cost 1612 for the selected marker-condition pair 1454. Based on this compact, concise, and easily managed summary and drill-down information provided by GUI 1200, the decision-maker may efficiently decide, on a per-specialty basis, which pairs of medical conditions and marker code groups represent the best area to devote education and training resources with respect to clinically supported process-of-care standards. For example, a relatively large number of indicators 1686 in a right-hand tail of actual utilization distribution graphic 1684, combined with a significant bundle cost 1692, may indicate that an efficient strategy would be general education and training across all providers, while a few large numbers in estimated monetary savings 1608 may indicate that an efficient strategy would be education and training targeted directly to the corresponding listed medical care providers 1604. In other examples, the user may utilize additional, fewer, and/or different steps than those described above, and/or may use the tools provided by GUI 1200 for purposes other than direction of education and training resources.

Although uses and advantages have been described above in terms of user interaction with the computer system 20 (shown in FIG. 11) through GUI 1200, it should be noted that in some examples, many or all of the above-described uses and advantages are also obtainable from other forms of interaction with computer system 20. Moreover, the structured outputs described above with respect to displays by GUI 1200 also provide many or all of the above-described advantages when presented in the form of stand-alone display screens or printouts, such as providing a decision-maker with an outcome of an objective, repeatable, clinically supported evaluation of medical care providers within a selected medical specialty in a concise, easily comprehended format that guides the decision-maker to a detailed understanding of the precise impact of underlying patterns of practice on the outcome, and/or guiding the decision-maker in the selection, understanding, and/or application of meaningful thresholds for more complex evaluations for medical care providers, such as a determination of whether to relax prior authorization rules for a particular medical care provider and/or an identification of precise areas for improvement that would make the medical care provider eligible for relaxation of prior authorization rules.

For example, in addition or alternatively to receiving input values through interaction with specialty control 1204, pass/fail highlight control 1240, and pass/fail threshold control 1252 in order to present pass/fail threshold tier 1302 via GUI 1200, computer system 20 is programmed to receive the corresponding values through a batch input file or command line input, and to output pass/fail threshold tier 1302 (e.g., protocol-range outlier table 1304 and/or plan-percentile outlier table 1354) as a standalone display screen and/or as a printout. In some examples, pass/fail threshold tier 1302 being output in these alternative forms still provides a compact, concise, advantageous tool that visually aids the decision-maker in selecting a relevant target point and a relevant outlier threshold for a given evaluation, as discussed above.

For another example, in addition or alternatively to receiving input values through interaction with utilization summary control 1254, target control 1320, outlier threshold control 1322, and qualifying-standard control 1326 in order to present providers summary display tier 1402 via GUI 1200, computer system 20 is programmed to receive the corresponding values through a batch input file or command line input, and to output providers summary display tier 1402 as a standalone display screen and/or as a printout. In some examples, providers summary display tier 1402 being output in these alternative forms still provides a specific, compact, advantageous distillation of the many thousands or millions of records in a typical CLI file that visually enables the decision-maker to compare and contrast the performance of a group of medical care provider using the specifically derived overall score 1406 (e.g., the simple overall score 1408 and/or the weighted overall score 1410) and the corresponding overall status (e.g., pass/fail), based on the selected configuration criteria, and further enables efficient selection of particular medical care providers for a "drill down" evaluation.

For another example, in addition or alternatively to receiving an interactive selection of one of the listed medical care providers 1404 on providers summary display tier 1402 in order to present provider detail display tier 1502 via GUI 1200, computer system 20 is programmed to receive the corresponding selection of one or more medical providers for a drill-down evaluation through a batch input file or command line input, and to output provider detail display tier 1502 as a standalone display screen and/or as a printout. In some examples, provider detail display tier 1502 being output in these alternative forms still provides a compact, concise tool that visually and procedurally aids the decision-maker in reviewing the provider's outlier status with respect to each marker-condition pair associated with the selected medical specialty, and in particular the estimated cost over-run for each "failed" marker-condition pair 1504, to evaluate whether the medical care provider merits relaxation of prior authorization rules in the specialty, and/or to present the medical care provider with an objective, concise, clinically supported set of objective goals (i.e., a set of marker-condition pairs and target points) that the medical provider needs to meet or improve upon in order to qualify for relaxation of prior authorization.

For another example, in addition or alternatively to receiving input values through interaction with utilization summary control 1254, target control 1320, outlier threshold control 1322, and qualifying-standard control 1326 in order to present services summary display tier 1452 via GUI 1200, computer system 20 is programmed to receive the corresponding values through a batch input file or command line input, and to output services summary display tier 1452 as a standalone display screen and/or as a printout. In some examples, services summary display tier 1452 being output in these alternative forms still provides a specific, compact, advantageous distillation of the many thousands or millions of records in a typical CLI file that visually enables the decision-maker to evaluate the aggregate performance (e.g., pass rate 1464) of a group of medical care providers for each marker-condition pair 1454 associated with the medical specialty, based on the selected configuration criteria, and further enables efficient selection of particular marker-condition pairs for a "drill down" evaluation.

For another example, in addition or alternatively to receiving an interactive selection of one of the listed marker-condition pairs 1454 on services summary display tier 1452 in order to present service detail display tier 1602 and/or actual utilization distribution graphic 1684 via GUI 1200, computer system 20 is programmed to receive the corresponding selection of one or more marker-condition pairs for a drill-down evaluation through a batch input file or command line input, and to output service detail display tier 1602 and/or actual utilization distribution graphic 1684 as a standalone display screen and/or as a printout. In some examples, service detail display tier 1602 and/or actual utilization distribution graphic 1684 being output in these alternative forms still provides a compact, concise tool that visually and procedurally aids the decision-maker in reviewing the estimated monetary savings 1608 associated with each medical care provider in the selected medical specialty with respected to the marker-condition pair of interest, the sum 1610 of the estimated monetary savings 1608 across the listing of qualifying medical care providers 1604, and/or the distribution of the actual rate of utilization across the listed medical care providers 1604, to determine a strategy for general or targeted education and training for some or all of the medical providers with respect to the marker-condition pair of interest.

In other examples, computer system 20 is programmed to implement any suitable combination of input interaction through aspects of GUI 1200, batch input file, command line input (e.g., either via text or voice recognition), or any other suitable input mechanism, and to implement any suitable combination of output presentation through aspects of GUI 1200, standalone display screen, printout, or any other suitable output mechanism, that enables computer system 20 to implement the methods of analysis and evaluation described herein.

Examples of a graphical user interface (GUI), computer-implemented method, and computer system for use in evaluating a plurality of medical care providers against process-of-care standards are described above in detail. The GUI, method and system are not limited to the specific examples described herein, but rather, components of the GUI and system and steps of the method may be used independently and separately from other components and environmental elements described herein.

When introducing elements of the present disclosure or the embodiment(s) thereof, the articles "a", "an", "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the disclosure, it is intended that all matter contained in the above description and shown in the accompanying drawings shall be interpreted as illustrative and not in a limiting sense.

What is claimed is:

1. A computer-implemented method for determining a significance of departure of a medical care provider from a plurality of process-of-care standards, the significance communicated at a granularity of specific procedures and services performed for specific medical conditions, the method implemented by at least one processor in communication with a memory device, a user input device, and a graphical user interface (GUI) on a display device, the method comprising steps executed by the at least one processor of:

retrieving a file of claim line item records numbering at least 100,000, each of the claim line item records corresponding to a claim submitted to a health plan and including: i) a code from among at least 100 codes corresponding to medical, surgical, and diagnostic procedures or services, ii) a patient identifier of a patient, and iii) a provider identifier of a medical care provider from among a plurality of medical care providers numbering at least 1,000;

reorganizing the file of claim line item records based on episodes of care, wherein each of the episodes of care includes the claim line item records for the medical, surgical, and diagnostic procedures or services used to treat a specific one of a plurality of medical conditions across a contiguous length of time for a specific patient, and wherein an episode identifier for the associated episode of care is added to each of the claim line item records;

storing the reorganized file of claim line item records;

retrieving an episode file that assigns episode identifiers for a non-outlier subset of the episodes of care to corresponding medical care providers;

retrieving, from a database, definitions for marker code groups, wherein each of the marker code groups comprises one or more related codes from among the at least 100 codes and is associated with a corresponding one of the plurality of medical conditions, and wherein each marker code group and the associated medical condition defines a marker-condition pair;

receiving user input at a service detail display displayed on the GUI in a first pane for selecting a medical care provider from among the plurality of medical care providers, the medical care provider associated with a medical specialty from among a plurality of medical specialties, each of the medical specialties associated in the database with a set of medical conditions from among the plurality of medical conditions and with marker-condition pairs associated with the set of medical conditions;

receiving user input at a target control displayed in a second pane for selecting a target point definition, the second pane being displayed along with the first pane;

receiving user input at a pass/fail threshold control displayed on the GUI in the first pane for selecting a threshold definition;

parsing the episode file to identify the episode identifiers assigned to the selected medical care provider for the non-outlier subset of the episodes of care for the set of medical conditions in the medical specialty associated with the selected medical care provider;

parsing the claim line item records in the stored reorganized file of claim line item records having the identified episode identifiers to determine an actual rate of utilization by the selected medical care provider of the marker code groups for each marker-condition pair in the medical specialty associated with the selected medical care provider;

retrieving, from the database, a protocol range for each marker-condition pair in the medical specialty associated with the selected medical care provider;

retrieving, from the database for each marker code group of the marker-condition pairs associated with the selected medical specialty, a bundle cost associated with a single utilization of the marker code group; and generating an output for display in the second pane by switching content displayed in the second pane while displaying the first pane, the generated output including:

a listing of the one or more marker-condition pairs associated with the selected medical specialty;

for each of the listed marker-condition pairs, a target point for a rate of utilization of the marker code group for the associated medical condition, wherein the target point is determined by applying, by the processor for each of the listed pairs, the target point definition to the retrieved protocol range associated with the pair;

for each of the listed marker-condition pairs, an indication of a status, wherein the status is selected from among a group comprising (i) a fail status, assigned in response to the actual rate of utilization by the selected medical care provider for the marker-condition pair exceeding the target rate of utilization, and (ii) a pass status, assigned in response to the actual rate of utilization by the selected medical care provider for the marker-condition pair not exceeding the target rate of utilization; and for each failed marker-condition pair, a calculated cost of overuse based on the bundle cost of the marker code group associated with the respective marker-condition pair and a difference between the actual rate of utilization for the marker-condition pair and the target rate of utilization for the marker-condition pair, wherein the cost of overuse communicates the significance of departures from the process-of-care standard for the associated marker-condition pair.

2. The method according to claim 1, further comprising:

aggregating the statuses for the selected medical care provider by calculating a ratio of a number of the marker-condition pairs having the pass status to a sum of the number of the marker-condition pairs having the pass status and a number of the marker-condition pairs having the fail status;

comparing, by the at least one processor, the ratio to a threshold ratio to obtain an overall score for the selected medical care provider; and including the overall score in the output.

3. The method according to claim 1, further comprising:

aggregating the statuses for the selected medical care provider by i) assigning a weighted status to each marker-condition pair, the weighted status proportionate to the bundle cost of the associated marker code group applied to a number of episodes of the corresponding medical condition for the selected medical care provider, and ii) calculating a ratio of an aggregate of the weighted status of the marker-condition pairs having the pass status to a sum of the aggregate of the weighted status of the marker-condition pairs having the pass status and an aggregate of the weighted status of the marker-condition pairs having the fail status;

comparing, by the at least one processor, the ratio to a threshold ratio to obtain an overall score for the selected medical care provider; and including the overall score in the output.

4. The method according to claim 1, wherein the actual rate of utilization is based on a percentage of the episodes of care for the corresponding medical condition attributable to the selected medical care provider in which any of the one or more related codes of the associated marker code group was utilized.

5. The method according to claim 1, wherein the actual rate of utilization is based on a total number of instances of utilization of any of the one or more related codes of the associated marker code group per a specified number of episodes of care of the associated medical condition.

6. The method according to claim 1, wherein the actual rate of utilization is based on a total cost of utilization of any of the one or more related codes of the associated marker code group per a specified number of the episodes of care of the associated medical condition.

7. The method according to claim 1, wherein the actual rate of utilization is based on a total number of instances of utilization of any of the one or more related codes of the associated marker code group per number of patients treated by the selected medical care provider.

8. The method according to claim 1, wherein the actual rate of utilization is based on a total cost of utilization of any of the one or more related codes of the associated marker code group per number of patients treated by the selected medical care provider.

9. The method according to claim 1, wherein the actual rate of utilization is based on one of i) a total number of instances of utilization of, or ii) a total cost of utilization of, any of the one or more related codes of the associated marker code group per number of members treated by the selected medical care provider, wherein a member is an individual to whom health care coverage has been extended under a health plan, and wherein treatment of a member comprises treatment of any of one or more individuals included in the member's health care coverage under the health plan.

10. A computer system for determining a significance of departure of a medical care provider from a plurality of process-of-care standards, the significance communicated at a granularity of specific procedures and services performed for specific medical conditions, the computer system comprising at least one processor in communication with a memory device storing instructions executable by the at least one processor to cause the at least one processor to perform steps of:

retrieving a file of claim line item records numbering at least 100,000, each of the claim line item records corresponding to a claim submitted to a health plan and including: i) a code from among at least 100 codes corresponding to medical, surgical, and diagnostic procedures or services, ii) a patient identifier of a patient, and iii) a provider identifier of a medical care provider from among a plurality of medical care providers numbering at least 1,000;

reorganizing the file of claim line item records based on episodes of care, wherein each of the episodes of care includes the claim line item records for the medical, surgical, and diagnostic procedures or services used to treat a specific one of a plurality of medical conditions across a contiguous length of time for a specific patient, and wherein an episode identifier for the associated episode of care is added to each of the claim line item records;

storing the reorganized file of claim line item records;

retrieving an episode file that assigns episode identifiers for a non-outlier subset of the episodes of care to corresponding medical care providers;

retrieving, from a database, definitions for marker code groups, wherein each of the marker code groups comprises one or more related codes from among the at least 100 codes and is associated with a corresponding one of the plurality of medical conditions, and wherein each marker code group and the associated medical condition defines a marker-condition pair;

receiving user input at a service detail display displayed on a graphical user interface (GUI) in a first pane for selecting a medical care provider from among the plurality of medical care providers, the medical care provider associated with a medical specialty from among a plurality of medical specialties, each of the medical specialties associated in the database with a set of medical conditions from among the plurality of medical conditions and with marker-condition pairs associated with the set of medical conditions;

receiving user input at a target control displayed in a second pane for selecting a target point definition, the second pane being displayed along with the first pane;

receiving user input at a pass/fail threshold control displayed on the GUI in the first pane for selecting a threshold definition;

parsing the episode file to identify the episode identifiers assigned to the selected medical care provider for the non-outlier subset of the episodes of care for the set of medical conditions in the medical specialty associated with the selected medical care provider;

parsing the claim line item records in the stored reorganized file of claim line item records having the identified episode identifiers to determine an actual rate of utilization by the selected medical care provider of the marker code groups for each marker-condition pair in the medical specialty associated with the selected medical care provider;

retrieving, from the database, a protocol range for each marker-condition pair in the medical specialty associated with the selected medical care provider;

retrieving, from the database for each marker code group of the marker-condition pairs associated with the selected medical specialty, a bundle cost associated with a single utilization of the marker code group; and generating an output for display in the second pane by switching content displayed in the second pane while displaying the first pane, the generated output including:

a listing of the one or more marker-condition pairs associated with the selected medical specialty;

for each of the listed marker-condition pairs, a target point for a rate of utilization of the marker code group for the associated medical condition, wherein the target point is determined by applying, by the processor for each of the listed pairs, the target point definition to the retrieved protocol range associated with the pair;

for each of the listed marker-condition pairs, an indication of a status, wherein the status is selected from among a group comprising (i) a fail status, assigned in response to the actual rate of utilization by the selected medical care provider for the marker-condition pair exceeding the target rate of utilization, and (ii) a pass status, assigned in response to the actual rate of utilization by the selected medical care provider for the marker-condition pair not exceeding the target rate of utilization; and for each failed marker-condition pair, a calculated cost of overuse based on the bundle cost of the marker code group associated with the respective marker-condition pair and a difference between the actual rate of utilization for the marker-condition pair and the target rate of utilization for the marker-condition pair, wherein the cost of overuse communicates the significance of departures from the process-of-care standard for the associated marker-condition pair.

11. The computer system according to claim 10, wherein the instructions are executable to further cause the at least processor to perform steps of:

aggregating the statuses for the selected medical care provider by calculating a ratio of a number of the marker-condition pairs having the pass status to a sum of the number of the marker-condition pairs having the pass status and a number of the marker-condition pairs having the fail status;

comparing, by the at least one processor, the ratio to a threshold ratio to obtain an overall score for the selected medical care provider; and including the overall score in the output.

12. The computer system according to claim 10, wherein the instructions are executable to further cause the at least processor to perform steps of:

aggregating the statuses for the selected medical care provider by i) assigning a weighted status to each marker-condition pair, the weighted status proportionate to the bundle cost of the associated marker code group applied to a number of episodes of the corresponding medical condition for the selected medical care provider, and ii) calculating a ratio of an aggregate of the weighted status of the marker-condition pairs having the pass status to a sum of the aggregate of the weighted status of the marker-condition pairs having the pass status and an aggregate of the weighted status of the marker-condition pairs having the fail status;

comparing, by the at least one processor, the ratio to a threshold ratio to obtain an overall score for the selected medical care provider; and including the overall score in the output.

13. The computer system according to claim 10, wherein the actual rate of utilization is based on a percentage of the episodes of care for the corresponding medical condition attributable to the selected medical care provider in which any of the one or more related codes of the associated marker code group was utilized.

14. The computer system according to claim 10, wherein the actual rate of utilization is based on a total number of instances of utilization of any of the one or more related codes of the associated marker code group per a specified number of episodes of care of the associated medical condition.

15. The computer system according to claim 10, wherein the actual rate of utilization is based on a total cost of utilization of any of the one or more related codes of the associated marker code group per a specified number of the episodes of care of the associated medical condition.

16. The computer system according to claim 10, wherein the actual rate of utilization is based on a total number of instances of utilization of any of the one or more related codes of the associated marker code group per number of patients treated by the selected medical care provider.

17. The computer system according to claim 10, wherein the actual rate of utilization is based on a total cost of utilization of any of the one or more related codes of the associated marker code group per number of patients treated by the selected medical care provider.

18. The computer system according to claim 10, wherein the actual rate of utilization is based on one of i) a total number of instances of utilization of, or ii) a total cost of utilization of, any of the one or more related codes of the associated marker code group per number of members treated by the selected medical care provider, wherein a member is an individual to whom health care coverage has been extended under a health plan, and wherein treatment of a member comprises treatment of any of one or more individuals included in the member's health care coverage under the health plan.

19. A non-transitory computer-readable medium containing computer-readable instructions for determining a significance of departure of a medical care provider from a plurality of process-of-care standards, the significance communicated at a granularity of specific procedures and services performed for specific medical conditions, wherein the instructions are executable by at least one processor to cause the at least one processor to perform steps of:

retrieving a file of claim line item records numbering at least 100,000, each of the claim line item records corresponding to a claim submitted to a health plan and including: i) a code from among at least 100 codes corresponding to medical, surgical, and diagnostic procedures or services, ii) a patient identifier of a patient, and iii) a provider identifier of a medical care provider from among a plurality of medical care providers numbering at least 1,000;

reorganizing the file of claim line item records based on episodes of care, wherein each of the episodes of care includes the claim line item records for the medical, surgical, and diagnostic procedures or services used to treat a specific one of a plurality of medical conditions across a contiguous length of time for a specific patient, and wherein an episode identifier for the associated episode of care is added to each of the claim line item records;

storing the reorganized file of claim line item records;

retrieving an episode file that assigns episode identifiers for a non-outlier subset of the episodes of care to corresponding medical care providers;

retrieving, from a database, definitions for marker code groups, wherein each of the marker code groups comprises one or more related codes from among the at least 100 codes and is associated with a corresponding one of the plurality of medical conditions, and wherein each marker code group and the associated medical condition defines a marker-condition pair;

receiving user input at a service detail display displayed on a graphical user interface (GUI) in a first pane for selecting a medical care provider from among the plurality of medical care providers, the medical care provider associated with a medical specialty from among a plurality of medical specialties, each of the medical specialties associated in the database with a set of medical conditions from among the plurality of medical conditions and with marker-condition pairs associated with the set of medical conditions;

receiving user input at a target control displayed in a second pane for selecting a target point definition, the second pane being displayed along with the first pane;

receiving user input at a pass/fail threshold control displayed on the GUI in the first pane for selecting a threshold definition;

parsing the episode file to identify the episode identifiers assigned to the selected medical care provider for the non-outlier subset of the episodes of care for the set of medical conditions in the medical specialty associated with the selected medical care provider;

parsing the claim line item records in the stored reorganized file of claim line item records having the identified episode identifiers to determine an actual rate of utilization by the selected medical care provider of the marker code groups for each marker-condition pair in the medical specialty associated with the selected medical care provider;

retrieving, from the database, a protocol range for each marker-condition pair in the medical specialty associated with the selected medical care provider;

retrieving, from the database for each marker code group of the marker-condition pairs associated with the selected medical specialty, a bundle cost associated with a single utilization of the marker code group; and generating an output for display in the second pane by switching content displayed in the second pane while displaying the first pane, the generated output including:
 a listing of the one or more marker-condition pairs associated with the selected medical specialty;
 for each of the listed marker-condition pairs, a target point for a rate of utilization of the marker code group for the associated medical condition, wherein the target point is determined by applying, by the processor for each of the listed pairs, the target point definition to the retrieved protocol range associated with the pair;
 for each of the listed marker-condition pairs, an indication of a status, wherein the status is selected from among a group comprising (i) a fail status, assigned in response to the actual rate of utilization by the selected medical care provider for the marker-condition pair exceeding the target rate of utilization, and (ii) a pass status, assigned in response to the actual rate of utilization by the selected medical care provider for the marker-condition pair not exceeding the target rate of utilization; and
 for each failed marker-condition pair, a calculated cost of overuse based on the bundle cost of the marker code group associated with the respective marker-condition pair and a difference between the actual rate of utilization for the marker-condition pair and the target rate of utilization for the marker-condition pair, wherein the cost of overuse communicates the significance of departures from the process-of-care standard for the associated marker-condition pair.

20. The non-transitory computer-readable medium according to claim 19, wherein the instructions are executable to further cause the at least processor to perform steps of:
 aggregating the statuses for the selected medical care provider by at least one of:
  calculating a ratio based on a number of the marker-condition pairs having the pass status and a sum of the number of the marker-condition pairs having the pass status and a number of the marker-condition pairs having the fail status; or
  i) assigning a weighted status to each marker-condition pair, the weighted status proportionate to the bundle cost of the associated marker code group applied to a number of episodes of the corresponding medical condition for the selected medical care provider, and ii) calculating the ratio based on an aggregate of the weighted status of the marker-condition pairs having the pass status and a sum of the aggregate of the weighted status of the marker-condition pairs having the pass status and an aggregate of the weighted status of the marker-condition pairs having the fail status;
 comparing, by the at least one processor, the ratio to a threshold ratio to obtain an overall score for the selected medical care provider; and
 including the overall score in the output.

* * * * *